United States Patent
Degering et al.

(10) Patent No.: US 12,415,973 B2
(45) Date of Patent: *Sep. 16, 2025

(54) HIGHLY ALKALINE TEXTILE DETERGENT COMPRISING PROTEASE

(71) Applicant: Henkel AG & Co. KGaA, Duesseldorf (DE)

(72) Inventors: Christian Degering, Erkrath (DE); Susanne Wieland, Zons/Dormagen (DE); Shohana Islam, Rheinbach (DE); Claudia Lindner, Solingen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 572 days.

This patent is subject to a terminal disclaimer.

(21) Appl. No.: 17/920,410

(22) PCT Filed: Mar. 23, 2021

(86) PCT No.: PCT/EP2021/057354
§ 371 (c)(1),
(2) Date: Oct. 21, 2022

(87) PCT Pub. No.: WO2021/219297
PCT Pub. Date: Nov. 4, 2021

(65) Prior Publication Data
US 2023/0159859 A1 May 25, 2023

(30) Foreign Application Priority Data

Apr. 29, 2020 (DE) ..................... 10 2020 205 381.2

(51) Int. Cl.
| | | |
|---|---|---|
| *C11D 3/386* | (2006.01) |
| *C11D 1/14* | (2006.01) |
| *C11D 1/22* | (2006.01) |
| *C11D 1/72* | (2006.01) |
| *C11D 1/83* | (2006.01) |
| *C11D 3/20* | (2006.01) |
| *C11D 3/36* | (2006.01) |
| *C11D 3/42* | (2006.01) |
| *C11D 3/50* | (2006.01) |
| *C12N 9/26* | (2006.01) |
| *C12N 9/54* | (2006.01) |

(52) U.S. Cl.
CPC ............ *C11D 3/38618* (2013.01); *C11D 1/83* (2013.01); *C11D 3/42* (2013.01); *C11D 3/50* (2013.01); *C12N 9/54* (2013.01); *C12Y 304/21062* (2013.01); *C11D 1/146* (2013.01); *C11D 1/22* (2013.01); *C11D 1/72* (2013.01); *C11D 2111/12* (2024.01)

(58) Field of Classification Search
None
See application file for complete search history.

(56) References Cited

U.S. PATENT DOCUMENTS

| | | |
|---|---|---|
| 4,071,377 A | 1/1978 | Schwuger et al. |
| 5,801,039 A | 9/1998 | Maurer et al. |
| 2004/0259222 A1 | 12/2004 | Breves et al. |
| 2005/0003419 A1 | 1/2005 | Breves et al. |
| 2009/0170745 A1 | 7/2009 | Merkel et al. |
| 2009/0275493 A1 | 11/2009 | Siegert et al. |
| 2012/0238005 A1 | 9/2012 | Wieland et al. |
| 2014/0227764 A1 | 8/2014 | Hellmuth et al. |
| 2016/0186159 A1 | 6/2016 | O'Connell et al. |
| 2016/0237418 A1 | 8/2016 | Hellmuth et al. |
| 2020/0172888 A1 | 6/2020 | Degering et al. |
| 2020/0172890 A1 | 6/2020 | Degering et al. |

FOREIGN PATENT DOCUMENTS

| | | |
|---|---|---|
| CN | 101945988 A | 1/2011 |
| CN | 103717724 A | 4/2014 |
| DE | 2412837 A1 | 10/1974 |
| DE | 102013221206 A1 | 4/2015 |
| EP | 2357220 A1 | 8/2011 |
| EP | 3660146 A1 | 6/2020 |
| EP | 3660151 A1 | 6/2020 |
| GB | 1243784 A | 8/1971 |

(Continued)

OTHER PUBLICATIONS

Search Report dated Jan. 21, 2021 from parallel German patent application No. 10 2020 205 381.2, 7 pages, for Information purpose only.

(Continued)

*Primary Examiner* — Manjunath N Rao
*Assistant Examiner* — Jae W Lee
(74) *Attorney, Agent, or Firm* — CANTOR COLBURN LLP

(57) ABSTRACT

The present disclosure relates to a textile detergent having at least one protease and a detergent ingredient for cleaning textiles by removing protease-sensitive stains. The protease may have proteolytic activity and include an amino acid sequence having at least 70% sequence identity with the amino acid sequence given in SEQ ID NO:1 over its entire length and, in each case based on the numbering according to SEQ ID NO:1. The protease may have amino acid substitutions at the positions corresponding to positions 3, 4, 99, or 199; and at least one additional amino acid substitution at at least one of the positions corresponding to positions 74, 136, 143, 154, 161, 163, 171, 200, 203, 209, 212 or 256. The textile detergent may have a pH ranging from approximately 9 to approximately 12, measured in a 1 wt. % solution in deionized water at 20° C.

12 Claims, No Drawings

Specification includes a Sequence Listing.

(56) References Cited

FOREIGN PATENT DOCUMENTS

| | | |
|---|---|---|
| WO | 9102792 A1 | 3/1991 |
| WO | 9221760 A1 | 12/1992 |
| WO | 9318140 A1 | 9/1993 |
| WO | 9523221 A1 | 8/1995 |
| WO | 9526397 A1 | 10/1995 |
| WO | 9623873 A1 | 8/1996 |
| WO | 9634946 A1 | 11/1996 |
| WO | 9923211 A1 | 5/1999 |
| WO | 0060060 A2 | 10/2000 |
| WO | 0144452 A1 | 6/2001 |
| WO | 0229024 A1 | 4/2002 |
| WO | 03002711 A2 | 1/2003 |
| WO | 03054177 A2 | 7/2003 |
| WO | 03057246 A1 | 7/2003 |
| WO | 2006002643 A2 | 1/2006 |
| WO | 2007079938 A2 | 7/2007 |
| WO | 2007131656 A1 | 11/2007 |
| WO | 2008007319 A2 | 1/2008 |
| WO | 2008086916 A1 | 7/2008 |
| WO | 2008112459 A2 | 9/2008 |
| WO | 2009102854 A1 | 8/2009 |
| WO | 2011032988 A1 | 3/2011 |
| WO | 2011100410 A2 | 8/2011 |
| WO | 2013003659 A1 | 1/2013 |
| WO | 2013016368 A1 | 1/2013 |
| WO | 2013060621 A1 | 5/2013 |
| WO | 2013063460 A2 | 5/2013 |
| WO | 2015036152 A1 | 3/2015 |
| WO | 2016096714 A1 | 6/2016 |

OTHER PUBLICATIONS

Search Report dated Jun. 24, 2021 from parallel international patent application No. PCT/EP2021/057354, 6 pages, for information purpose only.

Altschul et al., "Basic Local Alignment Seach Tool", 1990, pp. 403-410, 215, J. Mol. Biol., Academic Press Limited.

Altschul et al., "Gapped BLAST and PSI-BLAST: a new generation of protein database search programs", 1997, pp. 3389-3402, vol. 25, No. 17, Nucleic Acids Research.

Chenna et al., "Multiple sequence alignment with the Clustal series of programs", 2003, pp. 3497-3500, vol. 31, No. 13, Nucleic Acids Research, Oxford University Press.

Notredame et al., "T-Coffee: A Novel Method for Fast and Accurate Multiple Sequence Alignment", 2000, pp. 205-217, J. Mol. Biol., Academic Press.

Gornall et al., "Determination of Serum Proteins by Means of the Biuret Reaction", 1948, pp. 751-766, J. Biol. Chem.

Bender et al., "The Determination of the Concentration of Hydrolytic Enzyme Solutions: a-Chymotrypsin, Trypsin, Papain, Elastase, Subtilisin, and Acetylcholinesterase", 1966, pp. 5890-5913, Journal of the American Chemical Society, 88:24.

Jakob, "Engineering of subtilisin proteases for detergent applications", 2013, 79 pages, RWTH Aachen.

SEQUENCE LISTING

<160> NUMBER OF SEQ ID NOS: 4

<210> SEQ ID NO 1
<211> LENGTH: 269
<212> TYPE: PRT
<213> ORGANISM: Bacillus lentus

<400> SEQUENCE: 1

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
         35                  40                  45

Phe Val Pro Gly Glu Pro Ser Thr Gln Asp Gly Asn Gly His Gly Thr
     50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 2
<211> LENGTH: 485
<212> TYPE: PRT
<213> ORGANISM: Bacillus sp. 707

<400> SEQUENCE: 2

```
His His Asn Gly Thr Asn Gly Thr Met Met Gln Tyr Phe Glu Trp Tyr
 1               5                  10                  15

Leu Pro Asn Asp Gly Asn His Trp Asn Arg Leu Asn Ser Asp Ala Ser
             20                  25                  30

Asn Leu Lys Ser Lys Gly Ile Thr Ala Val Trp Ile Pro Pro Ala Trp
         35                  40                  45

Lys Gly Ala Ser Gln Asn Asp Val Gly Tyr Gly Ala Tyr Asp Leu Tyr
```

```
            50                  55                  60
Asp Leu Gly Glu Phe Asn Gln Lys Gly Thr Val Arg Thr Lys Tyr Gly
 65                  70                  75                  80

Thr Arg Ser Gln Leu Gln Ala Ala Val Thr Ser Leu Lys Asn Asn Gly
                 85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
                115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
                180                 185                 190

Thr Glu Asn Gly Asn Tyr Asp Tyr Leu Met Tyr Ala Asp Ile Asp Met
                195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
                260                 265                 270

Gly Ala Ile Glu Asn Tyr Leu Gln Lys Thr Asn Trp Asn His Ser Val
                275                 280                 285

Phe Asp Val Pro Leu His Tyr Asn Leu Tyr Asn Ala Ser Lys Ser Gly
                290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Glu Gln Gly Tyr Pro Ser Val Phe Tyr
                355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Ser Lys Trp Met Phe Val Gly Arg Asn Lys Ala Gly
                435                 440                 445

Gln Val Trp Ser Asp Ile Thr Gly Asn Arg Thr Gly Thr Val Thr Ile
                450                 455                 460

Asn Ala Asp Gly Trp Gly Asn Phe Ser Val Asn Gly Gly Ser Val Ser
465                 470                 475                 480
```

```
Ile Trp Val Asn Lys
            485

<210> SEQ ID NO 3
<211> LENGTH: 485
<212> TYPE: PRT
<213> ORGANISM: Bacillus sp.

<400> SEQUENCE: 3

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
 50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
```

```
                355                 360                 365
Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Asn Lys Trp Met Phe Val Gly Arg Asn Lys Ala Gly
                435                 440                 445

Gln Val Trp Thr Asp Ile Thr Gly Asn Arg Ala Gly Thr Val Thr Ile
                450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 4
<211> LENGTH: 485
<212> TYPE: PRT
<213> ORGANISM: Bacillus sp.

<400> SEQUENCE: 4

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
        130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
                180                 185                 190

Ser Glu Asn Gly Asn Tyr Asp Tyr Leu Met Tyr Ala Asp Val Asp Met
            195                 200                 205

Asp His Pro Glu Val Val Asn Glu Leu Arg Arg Trp Gly Glu Trp Tyr
        210                 215                 220

Thr Asn Thr Leu Asn Leu Asp Gly Phe Arg Ile Asp Ala Val Lys His
225                 230                 235                 240
```

```
Ile Lys Tyr Ser Phe Thr Arg Asp Trp Leu Thr His Val Arg Asn Ala
            245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
                340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
                420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
450                 455                 460

Asn Ala Asp Gly Trp Ala Asn Phe Ser Val Asn Gly Gly Ser Val Ser
465                 470                 475                 480

Ile Trp Val Lys Arg
            485
```

HIGHLY ALKALINE TEXTILE DETERGENT COMPRISING PROTEASE

CROSS-REFERENCE TO RELATED APPLICATION

The present application is a national stage entry according to 35 U.S.C. § 371 of PCT application No.: PCT/EP2021/057354 filed on Mar. 23, 2021; which claims priority to German patent application 10 2020 205 381.2 filed on Apr. 29, 2020; all of which are incorporated herein by reference in their entirety and for all purposes.

The content of the ASCII text file of the sequence listing named "P85081US_Sequence_protocol_subsequent_filing_EN.txt", which is 15 kb in size was created on Apr. 29, 2020; the sequence listing is electronically submitted via EFS-Web herewith and is herein incorporated by reference in its entirety.

TECHNICAL FIELD

The disclosure is in the field of detergents, in particular detergents comprising at least one enzyme. The disclosure relates to a textile detergent, in particular a liquid textile detergent, comprising at least one protease of which the amino acid sequence has been modified in particular with regard to use in textile detergents, and at least one detergent ingredient, the textile detergent having a pH of from approximately 9 to approximately 12. Also part of the disclosure are the corresponding washing methods, the use of the agents described herein and the use of proteases in textile detergents having a pH of from approximately 9 to approximately 12, and the use of proteases in textile detergents having a pH of from approximately 9 to approximately 12 for removing protease-sensitive stains on textiles.

BACKGROUND

The use of enzymes in detergents has been established in the prior art for decades. They are used to expand the performance range of the agents in question according to their special activities. These include in particular hydrolytic enzymes such as proteases, amylases, lipases and cellulases. The first three mentioned hydrolyze proteins, starch and fats and thus contribute directly to the removal of dirt. Cellulases are used in particular due to their effect on fabric. Another group of detergent enzymes are oxidative enzymes, in particular oxidases, which, optionally in conjunction with other components, are preferably used to bleach stains or to produce the bleaching agents in situ. In addition to these enzymes, which are subject to continuous optimization, other enzymes such as pectinases, β-glucanases, mannanases or other hemicellulases (glycosidases) are constantly being made available for use in detergents in particular in order to be able to optimally tackle specific stains, to hydrolyze specific vegetable polymers in particular.

Proteases are the longest-established enzymes contained practically all modern effective detergents. This makes them one of the technically most important enzymes of all. Of these, in turn, proteases of the subtilisin type (subtilases, subtilopeptidases, EC 3.4.21.62), which are serine proteases due to the catalytically active amino acids, are particularly important. They act as non-specific endopeptidases and hydrolyze any acid amide bonds that are inside peptides or proteins. Their optimum pH is usually in the alkaline range at roughly pH 9. An overview of this family is given, e.g., in the article "Subtilases: Subtilisin-like Proteases" by R. Siezen, pages 75-95 in "Subtilisin enzymes," published by R. Bott and C. Betzel, New York, 1996. Subtilases are formed naturally from microorganisms. In particular, the subtilisins formed and secreted by *Bacillus* species are the most significant group of subtilases.

Examples of the subtilisin proteases preferably used in detergents are the subtilisins BPN' and Carlsberg, the protease PB92, the subtilisins 147 and 309, the protease from *Bacillus lentus*, in particular from *Bacillus lentus* DSM 5483, subtilisin DY and the enzymes thermitase, proteinase K and the proteases TW3 and TW7, which can be classified as subtilases but no longer as subtilisins in the narrower sense, and variants of said proteases which have an amino acid sequence that has been modified with respect to the starting protease.

International patent applications WO 95/23221 A1, WO 92/21760 A1 and WO 2013/060621 A1 disclose variants of the protease from *Bacillus lentus* DSM 5483 which are suitable for use in detergents or cleaning agents. Furthermore, the international patent applications WO 2011/032988 A1 and WO 2016/096714 A1 and the European patent application EP 3044302 A1 disclose detergents and cleaning agents which contain variants of the protease from *Bacillus lentus* DSM 5483. The protease variants disclosed in these documents can, in addition to other positions, be modified at positions 3, 4, 99 and/or 199 in the numbering of the protease from *Bacillus lentus* DSM 5483 and, for example, have the amino acids 3T, 4I, 99E or 199I at said positions. However, combinations of further modifications, as described below, cannot be found in said documents. In particular, it is not clear from these documents that certain *Bacillus lentus* protease variants are suitable for use in highly alkaline textile detergents.

In general, only selected proteases are suitable for use in liquid, surfactant-containing preparations in any case. Many proteases do not exhibit sufficient catalytic performance in such preparations or they are not sufficiently stable. For the use of proteases in textile detergents, therefore, high catalytic activity and stability under wash-cycle conditions is particularly desirable.

Solid textile detergents typically have a pH of from approximately 8 to approximately 10, while liquid textile detergents can have a pH of from approximately 7 to approximately 9. Alkaline liquid detergents are relatively common and are particularly popular in North America. However, the alkaline pH makes it difficult to find suitable enzymes and to formulate them into alkaline liquid detergents, since the high pH can negatively affect not only the performance of the enzymes but also their storage stability. In addition, enzymes are generally less stable in liquid detergents when the detergents have a high water content.

Consequently, protease and surfactant-containing liquid formulations from the prior art are disadvantageous in that the proteases contained, under standard washing conditions (e.g., in a temperature range of from 20 to 40° C.), in particular at a higher pH, do not have satisfactory proteolytic activity or are not sufficiently storage-stable, and the formulations therefore do not exhibit optimal cleaning performance on protease-sensitive stains.

One goal in the development of detergent formulations is therefore to modify the contained enzymes selectively or randomly using methods known from the prior art and thus optimize them for use in detergents. These methods include, for example, point mutagenesis, deletion or insertion mutagenesis, or fusion with other proteins or protein fragments.

Although a number of proteases for detergents are known from the prior art, there is still a need for proteases for use in highly alkaline textile detergents, in particular liquid textile detergents having a pH of from approximately 9 to approximately 12.

The object was therefore to further improve the stability of proteases in highly alkaline textile detergents and thus the cleaning performance of textile detergents.

SUMMARY

Surprisingly, it has now been found that a protease as defined herein, or a protease sufficiently similar thereto (in terms of sequence identity), compared to conventional proteases and/or compared to the wild-type form (SEQ ID NO:1) and/or a starting variant (SEQ ID NO:2 from WO 2013/060621 A1), is improved in terms of its storage stability and is therefore particularly suitable for use in textile detergents having a pH of from approximately 9 to approximately 12.

The present disclosure therefore relates, in a first aspect, to a textile detergent comprising a) at least one protease, the protease having proteolytic activity and comprising an amino acid sequence which has at least 70% sequence identity with the amino acid sequence given in SEQ ID NO:1 over its entire length and, in each case based on the numbering according to SEQ ID NO:1, has (i) at least two of the positions that correspond to positions 3, 4, 99 or 199, at least two amino acid substitutions, in particular the amino acid substitutions 3T, 4I, 99E and 199I, and (ii) at least one of the positions that correspond to positions 74, 136, 143, 154, 161, 163, 171, 200, 203, 209, 212 or 256, at least one additional amino acid substitution, in particular selected from 74D, 74E, 74Q, 136Q, 143L, 143W, 143Y, 154D, 154Q, 161T, 163G, 171L, 200A, 200L, 200S, 200T, 203K, 203V, 203W, 209W, 212S, 212T, 256D, 256E and 256Q, and b) has at least one detergent ingredient, preferably in an amount of from 0.01 to 99.9 wt. %, the textile detergent having a pH of from approximately 9 to approximately 12, measured in a 1 wt. % solution in deionized water at 20° C. The detergent is preferably a liquid textile detergent. More preferably, the textile detergent has a pH in a range of from 9 to 12, in particular 9.5 to 11.5, more preferably from 10 to 11, particularly preferably a pH of pH 10 in a 1 wt. % solution in deionized water at 20° C.

Textile detergents also demonstrate performance advantages over other textile detergents in particular when the textile detergents contain at least one additional enzyme of the same or a different type, e.g., amylase, cellulase, lipase, mannanase or pectinase, the list of other enzymes being incomplete. It is therefore preferred that the textile detergents contain at least one additional enzyme of the same type (i.e., an additional protease) or of a different type. The detergent preferably comprises at least one amylase, the amylase having amylolytic activity and being selected from a) an α-amylase comprising an amino acid sequence which is at least 80% identical to the amino acid sequence given in SEQ ID NO:2 over its entire length and optionally has at least one amino acid substitution at one of the positions 172, 202, 208, 255 and 261 in the numbering according to SEQ ID NO:2, preferably selected from the group consisting of M202L, M202V, M202S, M202T, M202I, M202Q, M202W, S255N, R172Q and combinations thereof; and/or b) an α-Amylase comprising an amino acid sequence which is at least 60% identical to the amino acid sequence given in SEQ ID NO:3 over its entire length and optionally at least one amino acid substitution at one of the positions 9, 26, 30, 33, 82, 37, 106, 118, 128, 133, 149, 150, 160, 178, 182, 186, 193, 195, 202, 203, 214, 231,256, 257, 258, 269, 270, 272, 283, 295, 296, 298, 299, 303, 304, 305, 311,314, 315, 318, 319, 320, 323, 339, 345, 361, 378, 383, 419, 421, 437, 441, 444, 445, 446, 447, 450, 458, 461, 471, 482 and 484 and/or a deletion at one of positions 183 and 184 in the numbering according to SEQ ID NO: 3, preferably at least one amino acid substitution at one of the positions 9, 26, 149, 182, 186, 202, 257, 295, 299, 323, 339 and 345, and/or particularly preferably at least one amino acid substitution or deletion selected from the group consisting of R118K, D183*, G184*, N195F, R320K, R458K, and combinations thereof; and/or c) an α-Amylase comprising an amino acid sequence which is at least 90% identical to the amino acid sequence given in SEQ ID NO: 4 over its entire length and optionally has at least one substitution and/or deletion at one of positions 93, 116, 118, 129, 133, 134, 140, 142, 146, 147, 149, 151, 152, 169, 174, 183, 184, 186, 189, 193, 195, 197, 198, 200, 203, 206, 210, 212, 213, 235, 243, 244, 260, 262, 284, 303, 304, 320, 338, 347, 359, 418, 431, 434, 439, 447, 458, 469, 476 and 477 in the numbering according to SEQ ID NO:4, preferably amino acid deletions at the positions 183 and 184.

The disclosure further relates to a method for producing such a textile detergent and to a method for cleaning textiles, in which method a detergent is used.

The disclosure also relates to the use of such a textile detergent for cleaning textiles.

The disclosure also relates to the use of a protease which has at least 70% sequence identity with the amino acid sequence given in SEQ ID NO:1 over its entire length and, in each case based on the numbering according to SEQ ID NO:1, has (i) at least two of the positions that correspond to positions 3, 4, 99 or 199, at least two amino acid substitutions, in particular the amino acid substitutions 3T, 4I, 99E and 199I, and (ii) at least one of the positions that correspond to positions 74, 136, 143, 154, 161, 163, 171, 200, 203, 209, 212 or 256, at least one additional amino acid substitution, in particular selected from 74D, 74E, 74Q, 136Q, 143L, 143W, 143Y, 154D, 154Q, 161T, 163G, 171L, 200A, 200L, 200S, 200T, 203K, 203V, 203W, 209W, 212S, 212T, 256D, 256E and 256Q, in a textile detergent, preferably a liquid textile detergent, for removing protease-sensitive stains from textiles, the textile detergent having a pH of from approximately 9 to approximately 12, measured in a 1 wt. % solution in deionized water at 20° C.

A protease is particularly preferably used in the agents, methods and uses which has at least 70% sequence identity with the amino acid sequence given in SEQ ID NO:1 over its entire length and, in each case based on the numbering according to SEQ ID NO:1, has (i) at the positions that correspond to positions 3, 4, 99 or 199, the amino acid substitutions S3T, V4I, R99E and V199I and (ii) at at least one of the positions that correspond to positions 74, 136, 143, 154, 161, 163, 171, 200, 203, 209, 212 or 256, at least one additional amino acid substitution selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, 256D, L256E and L256Q.

These and other aspects, features, and advantages will become apparent to a person skilled in the art through the study of the following detailed description and claims. Any feature from one aspect can be used in any other aspect. Furthermore, it will readily be understood that the examples contained herein are intended to describe and illustrate, but not to limit, the invention and that, in particular, the invention is not limited to these examples.

DETAILED DESCRIPTION

Unless indicated otherwise, all percentages are indicated in terms of weight percent (wt. %).

Numerical ranges that are indicated in the format "from x to y" also include the stated values. If several preferred numerical ranges are indicated in this format, it is readily understood that all ranges that result from the combination of the various endpoints are also included.

"At least one," as used herein, means one or more, i.e., 1, 2, 3, 4, 5, 6, 7, 8, 9, 10, 11, 12, 13, 14 or more.

The term "detergent," as used herein, is synonymous with the term "textile detergent" or "agent" and denotes a composition for cleaning textiles as explained in the description.

"Approximately," "about," or "roughly," as used herein in reference to a numerical value, refer to the corresponding numerical value±10%, preferably ±5%.

"Liquid," as used herein, includes liquids and gels as well as pasty compositions. It is preferred that the liquid compositions are flowable and pourable at room temperature, but it is also possible for them to have a limit of liquidity.

"Highly alkaline," as used herein, means a pH of from approximately 9 to approximately 12, measured in a 1 wt. % solution in deionized water at 20° C.

The present disclosure is based on the surprising finding by the inventors that amino acid substitutions at the positions described herein bring about improved storage stability of this modified protease in highly alkaline detergents compared to conventional proteases and/or compared to the wild type and/or compared to a starting variant which has already been improved compared to the wild type.

This is particularly surprising insofar as no such proteases or no such amino acid substitutions have previously been associated with improved storage stability of the corresponding protease in highly alkaline detergents, in particular liquid highly alkaline detergents.

In preferred embodiments, the modification(s) of the proteases used, in each case based on the numbering according to SEQ ID NO:1, (i) at at least two of the positions that correspond to positions 3, 4, 99 or 199, and (ii) at at least one of the positions that correspond to positions 74, 136, 143, 154, 161, 163, 171, 200, 203, 209, 212 or 256, lead(s) to improved storage stability of this modified protease in highly alkaline textile detergents (pH 9 to 12).

In other preferred embodiments of the proteases used, the protease, in each case based on the numbering according to SEQ ID NO:1, has (i) at at least two of the positions that correspond to positions 3, 4, 99 or 199, at least two amino acid substitutions which are selected from the group consisting of S3T, V4I, R99E and V199I, and (ii) at at least one of the positions that correspond to positions 74, 136, 143, 154, 161, 163, 171, 200, 203, 209, 212 or 256, at least one amino acid substitution selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q.

In preferred embodiments, the protease used, in each case based on the numbering according to SEQ ID NO:1, has (i) at at least two of the positions that correspond to positions 3, 4, 99 or 199, at least two amino acid substitutions selected from the group consisting of S3T, V4I, R99E and V199I, and (ii) at at least one of the positions that correspond to positions 74, 136, 143, 154, 161, 163, 171, 200, 203, 209, 212 or 256, at least one amino acid substitution selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q, the combination of the at least two amino acid substitutions from group (i) and the at least one amino acid substitution from group (ii) leading to improved storage stability of this modified protease in highly alkaline textile detergents (pH 9 to 12).

In particularly preferred embodiments, the detergent contains a protease having one of the following amino acid substitution variants:
(i) S3T+V4I+R99E+V199I+Q200L+Y203W;
(ii) S3T+V4I+R99E+V199I+N212S;
(iii) S3T+V4I+R99E+V199I+N74D;
(iv) S3T+V4I+R99E+V199I+S154D+L256E;
(v) S3T+V4I+R99E+V199I+Q200L+Y203W+S154D+L256E;
(vi) S3T+V4I+R99E+V199I+N74D+Q200L+Y203W;
(vii) S3T+V4I+R99E+V199I+N74D+S154D+Q200L+Y203W+L256E;
(viii) S3T+V4I+R99E+V199I+N74D+N212S;
(ix) S3T+V4I+R99E+V199I+N74D+S154D+Y203W+L256E;
(x) S3T+V4I+R99E+V199I+N74D+Y203W;
(xi) S3T+V4I+R99E+V199I+N74D+S154D+Q200L+L256E;
(xii) S3T+V4I+R99E+V199I+N74D+Q200L;
(xiii) S3T+V4I+R99E+V199I+S154D+Q200L+Y203W;
(xiv) S3T+V4I+R99E+V199I+Q200L+Y203W+L256E;
(xv) S3T+V4I+R99E+V199I+A136Q+R143W+Y161T+Q200L;
(xvi) S3T+V4I+R99E+V199I+N74D+R143Y+A209W+N212S+L256E;
(xvii) S3T+V4I+R99E+V199I+A136Q+S154D+V171L+Q200L,
the numbering being based in each case on the numbering according to SEQ ID NO:1.

Certain embodiments of the proteases used have improved storage stability. They have increased stability in highly alkaline textile detergents in comparison with conventional proteases and/or with the wild-type enzyme (SEQ ID NO:1) and/or with a starting variant of the protease (SEQ ID NO:2 from WO 2013/060621 A1), in particular when stored for 3 or more days, 4 or more days, 7 or more days, 10 or more days, 12 or more days, 14 or more days, 21 or more days or 28 or more days, the textile detergent having a pH of from approximately 9 to approximately 12, measured in 1 wt. % solution in deionized water at 20° C.

Certain embodiments of the proteases can have increased catalytic activity in highly alkaline textile detergents, independently of or in addition to the increased storage stability. In many embodiments, the proteases used can have proteolytic activity that is at least 101%, 102%, 103%, 104%, 105%, 106%, 107%, 108%, 109% or 110% based on the wild type (SEQ ID NO:1) and/or an already performance-enhanced starting variant (SEQ ID NO:2 from WO 2013/060621 A1). Such performance-enhanced proteases allow improved washing results on protease-sensitive stains in various temperature ranges, in particular in a temperature range of from 20 to 40° C.

Preferred embodiments of proteases used are furthermore particularly stable in detergents, for example with respect to surfactants and/or bleaching agents and/or chelators, and/or with respect to temperature effects, in particular with respect to high temperatures of, for example, between 50 and 65° C., in particular 60° C., and/or with respect to changes in pH and/or with respect to denaturing or oxidizing agents and/or with respect to proteolytic breakdown and/or with respect to a change in redox ratios. Performance-enhanced protease variants and/or protease variants with increased temperature stability are therefore provided by particularly preferred embodiments. Performance-enhanced protease variants and/or protease variants with increased temperature stability are provided by further particularly preferred embodiments. Such advantageous embodiments of proteases therefore allow improved washing results on protease-sensitive stains in a wide temperature range.

The proteases used exhibit enzymatic activity, i.e., they are capable of hydrolyzing peptides and proteins, in particular in detergents. A protease used is therefore an enzyme which catalyzes the hydrolysis of amide/peptide bonds in protein/peptide substrates and is thus able to cleave proteins or peptides. Furthermore, a protease is preferably a mature protease, i.e., the catalytically active molecule without signal peptide(s) and/or propeptide(s). Unless stated otherwise, the sequences specified also each refer to mature (processed) enzymes.

In various embodiments, the protease used is a free enzyme. This means that the protease can act directly with all the components of an agent and, if the agent is a liquid agent, that the protease is in direct contact with the solvent of the agent (e.g., water). In other embodiments, an agent may contain proteases that form an interaction complex with other molecules or that contain a "coating." In this case, an individual protease molecule or a plurality of protease molecules may be separated from the other constituents of the agent by a surrounding structure. Such a separating structure may arise from, but is not limited to, vesicles such as a micelle or a liposome. The surrounding structure may also be a virus particle, a bacterial cell or a eukaryotic cell. In various embodiments, an agent may include cells of *Bacillus pumilus* or *Bacillus gibsonii* or *Bacillus subtilis* which express the proteases, or cell culture supernatants of such cells.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence given in SEQ ID NO:1 over its entire length, and, in each case based on the numbering according to SEQ ID NO:1, has (i) at least two amino acid substitutions at at least two of the positions that correspond to positions 3, 4, 99 or 199, the at least two amino acid substitutions being selected from the group consisting of S3T, V4I, R99E and V199I, and (ii) at least one amino acid substitution at at least one of the positions that correspond to positions 74, 136, 143, 154, 161, 163, 171, 200, 203, 209, 212 or 256, the at least one amino acid substitution being selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98% and 98.5% identical to the amino acid sequence given in SEQ ID NO:1 over its entire length, and, in each case based on the numbering according to SEQ ID NO:1, has (i) at least three amino acid substitutions at at least three of the positions that correspond to positions 3, 4, 99 or 199, the at least three amino acid substitutions being selected from the group consisting of S3T, V4I, R99E and V199I, and (ii) at least one amino acid substitution at at least one of the positions that correspond to positions 74, 136, 143, 154, 161, 163, 171, 200, 203, 209, 212 or 256, the at least one amino acid substitution being selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5% and 98% identical to the amino acid sequence given in SEQ ID NO:1 over its entire length, and, in each case based on the numbering according to SEQ ID NO:1, has (i) the amino acid substitutions S3T, V4I, R99E and V199I, and (ii) at least one amino acid substitution at at least one of the positions that correspond to positions 74, 136, 143, 154, 161, 163, 171, 200, 203, 209, 212 or 256, the at least one amino acid substitution being selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98% and 98.5% identical to the amino acid sequence given in SEQ ID NO:1 over its entire length, and, in each case based on the numbering according to SEQ ID NO:1, has (i) at least two amino acid substitutions at at least two of the positions that correspond to positions 3, 4, 99 or 199, the at least two amino acid substitutions being selected from the group consisting of S3T, V4I, R99E and V199I, and (ii) at least two amino acid substitutions at at least two of the positions that correspond to positions 74, 136, 143, 154, 161, 163, 171, 200, 203, 209, 212 or 256, the at least two amino acid substitutions being selected from the group consisting of N74E, N74Q, A136Q, R143L, R143W, R143Y, S154D, S154Q, Y161T, A163G, V171L, Q200A, Q200A, Q200L, Q200S, Q200T, Y203K, Y203V, Y203W, A209W, N212S, N212T, L256D, L256E and L256Q.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5% and 98% identical to the amino acid sequence given in SEQ ID NO:1 over its entire length, and, in each case based on the numbering according to SEQ ID NO:1, has (i) at least three amino acid substitutions at least three of the positions that correspond to positions 3, 4, 99 or 199, the at least three amino acid substitutions being selected from the group consisting of S3T, V4I, R99E and V199I, and (ii) at least three amino acid substitutions at at least two of the positions that correspond to positions 74, 136, 143, 154, 161, 163, 171, 200, 203, 209, 212 or 256, the at least two amino acid substitutions being selected from the group consisting of N74E, N74Q, A136Q, R143L, R143W, R143Y, S154D, S154Q, Y161T, A163G, V171L, Q200A, Q200A, Q200L, Q200S, Q200T, Y203K, Y203V, Y203W, A209W, N212S, N212T, L256D, L256E and L256Q.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, and 97.5% identical to the amino acid sequence given in SEQ ID NO:1 over its entire length, and, in each case based on the numbering according to SEQ ID NO:1, has (i) the amino acid substitutions S3T, V4I, R99E and V199I, and (ii) at least two amino acid substitutions at at least two of the positions that correspond to positions 74, 136, 143, 154, 161, 163, 171, 200, 203, 209, 212 or 256, the at least two amino acid substitutions being selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, and 98% identical to the amino acid sequence given in SEQ ID NO:1 over its entire length, and, in each case based on the numbering according to SEQ ID NO:1, has (i) at least two amino acid substitutions at at least two of the positions that correspond to positions 3, 4, 99 or 199, the at least two amino acid substitutions being selected from the group consisting of S3T, V4I, R99E and V199I, and (ii) at least three amino acid substitutions at at least three of the positions that correspond to positions 74, 136, 143, 154, 161, 163, 171, 200, 203, 209, 212 or 256, the at least three amino acid substitutions being selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97% and 97.5% identical to the amino acid sequence given in SEQ ID NO:1 over its entire length, and, in each case based on the numbering according to SEQ ID NO:1, has (i) at least three amino acid substitutions at at least three of the positions that correspond to positions 3, 4, 99 or 199, the at least three amino acid substitutions being selected from the group consisting of S3T, V4I, R99E and V199I, and (ii) at least three amino acid substitutions at at least three of the positions that correspond to positions 74, 136, 143, 154, 161, 163, 171, 200, 203, 209, 212 or 256, the at least three amino acid substitutions being selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5% and 97% identical to the amino acid sequence given in SEQ ID NO:1 over its entire length, and, in each case based on the numbering according to SEQ ID NO:1, has (i) the amino acid substitutions S3T, V4I, R99E and V199I, and (ii) at least three amino acid substitutions at at least three of the positions that correspond to positions 74, 136, 143, 154, 161, 163, 171, 200, 203, 209, 212 or 256, the at least three amino acid substitutions being selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97% and 97.5% identical to the amino acid sequence given in SEQ ID NO:1 over its entire length, and, in each case based on the numbering according to SEQ ID NO:1, has (i) at least two amino acid substitutions at at least two of the positions that correspond to positions 3, 4, 99 or 199, the at least two amino acid substitutions being selected from the group consisting of S3T, V4I, R99E and V199I, and (ii) at least four amino acid substitutions at at least four of the positions that correspond to positions 74, 136, 143, 154, 161, 163, 171, 200, 203, 209, 212 or 256, the at least four amino acid substitutions being selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5% and 97% identical to the amino acid sequence given in SEQ ID NO:1 over its entire length, and, in each case based on the numbering according to SEQ ID NO:1, has (i) at least three amino acid substitutions at at least three of the positions that correspond to positions 3, 4, 99 or 199, the at least three amino acid substitutions being selected from the group consisting of S3T, V4I, R99E and V199I, and (ii) at least four amino acid substitutions at at least four of the positions that correspond to positions 74, 136, 143, 154, 161, 163, 171, 200, 203, 209, 212 or 256, the at least four amino acid substitutions being selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q.

In preferred embodiments, the protease used comprises an amino acid sequence which is at least 70% and, in order of increasing preference, at least 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5% and 97% identical to the amino acid sequence given in SEQ ID NO:1 over its entire length, and, in each case based on the numbering according to SEQ ID NO:1, has (i) the amino acid substitutions S3T, V4I, R99E and V199I, and (ii) at least four amino acid substitutions at at least four of the positions that correspond to positions 74, 136, 143, 154, 161, 163, 171, 200, 203, 209, 212 or 256, the at least four amino acid substitutions being selected from the group consisting of N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, L256D, L256E and L256Q.

In particularly preferred embodiments, the protease used contains one of the following amino acid substitution variants:
 (i) S3T+V4I+R99E+V199I+Q200L+Y203W;
 (ii) S3T+V4I+R99E+V199I+N212S;
 (iii) S3T+V4I+R99E+V199I+N74D;
 (iv) S3T+V4I+R99E+V199I+S154D+L256E;
 (v) S3T+V4I+R99E+V199I+Q200L+Y203W+S154D+L256E;
 (vi) S3T+V4I+R99E+V199I+N74D+Q200L+Y203W;
 (vii) S3T+V4I+R99E+V199I+N74D+S154D+Q200L+Y203W+L256E;
 (viii) S3T+V4I+R99E+V199I+N74D+N212S;
 (ix) S3T+V4I+R99E+V199I+N74D+S154D+Y203W+L256E;
 (x) S3T+V4I+R99E+V199I+N74D+Y203W;
 (xi) S3T+V4I+R99E+V199I+N74D+S154D+Q200L+L256E;
 (xii) S3T+V4I+R99E+V199I+N74D+Q200L;
 (xiii) S3T+V4I+R99E+V199I+S154D+Q200L+Y203W;
 (xiv) S3T+V4I+R99E+V199I+Q200L+Y203W+L256E;
 (xv) S3T+V4I+R99E+V199I+A136Q+R143W+Y161T+Q200L;
 (xvi) S3T+V4I+R99E+V199I+N74D+R143Y+A209W+N212S+L256E;
 (xvii) S3T+V4I+R99E+V199I+A136Q+S154D+V171L+Q200L,
the numbering being based in each case on the numbering according to SEQ ID NO:1.

In the context of the present disclosure, the feature whereby a protease has at least one of the given amino acid substitutions means that it contains one (of the given) amino acid substitution(s) at the relevant position, i.e., at least the given positions are not otherwise mutated or deleted, for example by fragmentation of the protease.

The identity of nucleic acid or amino acid sequences is determined by a sequence comparison. This sequence comparison is based on the BLAST algorithm established and commonly used in the prior art (cf., e.g., Altschul et al. (1990) "Basic local alignment search tool," J. Mol. Biol. 215:403-410, and Altschul et al. (1997): "Gapped BLAST and PSI-BLAST: a new generation of protein database search programs," Nucleic Acids Res., 25:3389-3402) and occurs in principle by similar sequences of nucleotides or amino acids in the nucleic acid or amino acid sequences being assigned to one another. A tabular assignment of the positions concerned is referred to as alignment. Another algorithm available in the prior art is the FASTA algorithm. Sequence comparisons (alignments), in particular multiple sequence comparisons, are created using computer programs. The Clustal series (cf., e.g., Chenna et al. (2003) "Multiple sequence alignment with the Clustal series of programs," Nucleic Acid Res. 31:3497-3500), T-Coffee (cf., e.g., Notredame et al. (2000) "T-Coffee: A novel method for multiple sequence alignments," J. Mol. Biol. 302:205-217) or programs based on these programs or algorithms, for example, are frequently used. Sequence comparisons (alignments) using the computer program Vector NTI® Suite 10.3 (Invitrogen Corporation, 1600 Faraday Avenue, Carlsbad, California, USA) with the predetermined standard parameters, the AlignX module of which program for the sequence comparisons is based on ClustalW, are also possible. Unless stated otherwise, the sequence identity specified herein is determined by the BLAST algorithm.

Such a comparison also allows conclusions to be drawn regarding the similarity of the compared sequences. It is usually indicated in percent identity, i.e., the proportion of identical nucleotides or amino acid functional groups in said sequences or in an alignment of corresponding positions. The broader concept of homology takes conserved amino acid exchanges into account in the case of amino acid sequences, i.e., amino acids having similar chemical activity, since they usually perform similar chemical activities within the protein. Therefore, the similarity of the compared sequences may also be stated as percent homology or percent similarity. Identity and/or homology information can be provided regarding whole polypeptides or genes or only regarding individual regions. Homologous or identical regions of different nucleic acid or amino acid sequences are therefore defined by matches in the sequences. Such regions often have identical functions. They can be small and comprise only a few nucleotides or amino acids. Often, such small regions perform essential functions for the overall activity of the protein. It may therefore be expedient to relate sequence matches only to individual, optionally small, regions. Unless stated otherwise, however, identity or homology information in the present application relates to the entire length of the particular nucleic acid or amino acid sequence indicated.

In the context of the present disclosure, the indication that an amino acid position corresponds to a numerically designated position in SEQ ID NO:1 therefore means that the corresponding position is associated with the numerically designated position in SEQ ID NO:1 in an alignment as defined above.

For the description of substitutions relating to exactly one amino acid position (amino acid exchanges), the following convention is used herein: first, the naturally occurring amino acid is designated in the form of the internationally used one-letter code, followed by the associated sequence position and finally the inserted amino acid. A plurality of exchanges within the same polypeptide chain are separated by slashes. For insertions, additional amino acids are named following the sequence position. In the case of deletions, the missing amino acid is replaced by a symbol, for example a star or a dash, or a Δ is indicated before the corresponding position. For example, A95G describes the substitution of alanine at position 95 by glycine, A95AG describes the insertion of glycine after the amino acid alanine at position 95, and A95* or ΔA59 describes the deletion of alanine at position 95. This nomenclature is known to a person skilled in the art of enzyme technology.

The present disclosure also relates to a detergent comprising a protease, characterized in that the protease can be obtained from a protease as the starting molecule by one or more conservative amino acid substitutions. The term "conservative amino acid substitution" means the exchange (substitution) of one amino acid functional group for another amino acid functional group, with this exchange not resulting in a change to the polarity or charge at the position of the exchanged amino acid, e.g., the exchange of a nonpolar amino acid functional group for another nonpolar amino acid functional group. Conservative amino acid substitutions include, for example: G=A=S, I=V=L=M, D=E, N=Q, K=R, Y=F, S=T, G=A=I=V=L=M=Y=F=W=P=S=T.

The present disclosure also relates to a detergent comprising a protease, characterized in that the protease can be obtained from a protease as a starting molecule by fragmentation, deletion, insertion or substitution mutagenesis and comprises an amino acid sequence which matches the starting molecule over a length of at least 190, 200, 210, 220, 230, 240, 250, 260, 261, 262, 263, 264, 265, 266, 267, 268 or 269 contiguous amino acids, the protease (i) having at least two amino acid substitutions at at least two of the positions that correspond to positions 3, 4, 99 or 199, and (ii) at at least one amino acid substitution at at least one of the positions that correspond to positions 74, 136, 143, 154, 161, 163, 171, 200, 203, 209, 212 or 256.

delete without the proteolytic activity being lost or diminished thereby. Furthermore, such fragmentation, deletion mutagenesis, insertion mutagenesis or substitution mutagenesis can also, for example, reduce the allergenicity of the enzymes in question and thus improve their overall applicability. Advantageously, the enzymes retain their proteolytic activity even after mutagenesis, i.e., their proteolytic activity corresponds at least to that of the starting enzyme, i.e., in a preferred embodiment the proteolytic activity is at least 80%, preferably at least 90% of the activity of the starting enzyme. Other substitutions can also exhibit advantageous effects. Both single and a plurality of contiguous amino acids can be exchanged for other amino acids.

The amino acid positions are in this case defined by an alignment of the amino acid sequence of a protease with the amino acid sequence of the protease from *Bacillus lentus*, as given in SEQ ID NO:1. Furthermore, the assignment of the positions depends on the mature protein. This assignment is also to be used in particular if the amino acid sequence of a protease comprises a higher or lower number of amino acid functional groups than the protease from *Bacillus lentus* according to SEQ ID NO:1. Proceeding from the mentioned positions in the amino-acid sequence of the protease from *Bacillus lentus*, the modification positions in a protease are those which are precisely assigned to these positions in an alignment.

Further confirmation of the correct assignment of the amino acids to be modified, i.e., in particular their functional correspondence, can be provided by comparative tests, according to which the two positions assigned to one another on the basis of an alignment are modified in the same way in both compared proteases, and observations are made as to whether the enzymatic activity is modified in the same way in both cases. If, for example, an amino acid exchange in a specific position of the protease according to SEQ ID NO:1 is accompanied by a modification of an enzymatic parameter, for example an increase in the KM value, and a corresponding alteration of the enzymatic parameter, for example likewise an increase in the KM value, is observed in a protease variant of which the amino acid exchange has been achieved by the same introduced amino acid, this can therefore be considered to be confirmation of the correct assignment.

A protease can additionally be stabilized, in particular by one or more mutations, for example substitutions, or by coupling to a polymer. An increase in stability during storage and/or during use, for example in the washing process, leads to longer enzymatic activity and thus improves the cleaning performance. In principle, all stabilization options which are described in the prior art and/or are appropriate are considered. The stabilizations which are achieved by mutations of the enzyme itself are preferred, since such stabilizations do not require any further work steps following the recovery of the enzyme. Further possibilities for stabilization are, e.g.:

altering the binding of metal ions, in particular the calcium binding sites, for example by exchanging one or more of the amino acid(s) that are involved in the calcium binding with one or more negatively charged amino acids and/or by introducing sequence alterations in at least one of the sequences of the two amino acids arginine and glycine;

protecting against the influence of denaturing agents such as surfactants by mutations that cause a modification of the amino acid sequence on or at the surface of the protein;

exchanging amino acids near the N-terminus with those likely to contact the rest of the molecule via non-covalent interactions, thus contributing to the maintenance of the globular structure.

Preferred embodiments are those in which the enzyme is stabilized in several ways since a plurality of stabilizing mutations act additively or synergistically.

The disclosure also relates to a protease as described above, which is characterized in that it has at least one chemical modification. A protease having such a modification is referred to as a derivative, i.e., the protease is derivatized. In the context of the present application, derivatives are thus understood to mean those proteins of which the pure amino acid chain has been chemically modified. Such derivatizations can be achieved, e.g., in vivo by the host cell that expresses the protein. In this regard, couplings of low-molecular-weight compounds such as lipids or oligosaccharides are particularly noteworthy. However, the derivatizations may also be carried out in vitro, for example by the chemical conversion of a side chain of an amino acid or by covalent bonding of another compound to the protein. For example, it is possible to couple amines to carboxyl groups of an enzyme in order to alter the isoelectric point. Another such compound may also be another protein that is bound to a protein via bifunctional chemical compounds, for example. Derivatization is likewise understood to mean the covalent bonding to a macromolecular carrier or also a non-covalent inclusion in suitable macromolecular cage structures. Derivatizations may, e.g., affect the substrate specificity or bonding strength to the substrate or cause a temporary blockage of the enzymatic activity when the coupled substance is an inhibitor. This can be expedient, e.g., for the period of storage. Such modifications may further affect the stability or enzymatic activity. They can also be used to reduce the allergenicity and/or immunogenicity of the protein and for example increase its skin compatibility. For example, couplings with macromolecular compounds, for example polyethylene glycol, can improve the protein in terms of stability and/or skin compatibility. Derivatives of a protein can also be understood in the broadest sense to mean preparations of these proteins. Depending on the recovery, processing or preparation, a protein can be associated with various other substances, e.g., from the culture of the producing microorganisms. A protein may also have been deliberately added to other substances, e.g., to increase its storage stability. Therefore, all preparations of a protein are also in accordance with the disclosure. This is also irrespective of whether or not it actually exhibits this enzymatic activity in a particular preparation. This is because it may be desired that it has no or only low activity during storage, and exhibits its enzymatic function only at the time of use. This can be controlled via appropriate accompanying substances, for example. In particular, the joint preparation of proteases with specific inhibitors is possible in this regard.

Of all the proteases or protease variants and/or derivatives described above, particular preference is given to those of which the storage stability and/or cleaning performance is improved compared to the starting variant, with the cleaning performance in a washing system being determined as described below.

Numerous proteases and in particular subtilisins are formed as so-called preproteins, i.e., together with a propeptide and a signal peptide, where the function of the signal peptide is usually to ensure the release of the protease from the cell producing it into the periplasm or the medium surrounding the cell, and the propeptide is usually necessary for the protease to fold correctly. The signal peptide and the propeptide are usually the N-terminal part of the preprotein. The signal peptide is cleaved off from the rest of the protease under natural conditions by a signal peptidase. The correct final folding of the protease, supported by the propeptide, then takes place. The protease is then in its active form and cleaves off the propeptide itself. After the propeptide has been cleaved off, the then-mature protease, in particular subtilisin, carries out its catalytic activity without the N-terminal amino acids originally present. For technical applications in general and in particular, the mature proteases, i.e., the enzymes processed after their production, are preferred over the preproteins. The proteases can also be modified by the cells producing them after the production of the polypeptide chain, for example by attaching sugar molecules, formylations or aminations, etc. Such modifications are post-translational modifications and can, but do not have to, have an influence on the function of the protease.

"Variant," as used herein, refers to naturally or artificially generated variations of a native protease which has an amino acid sequence which is modified from the reference form. In addition to the amino acid alterations discussed above, proteases can have other amino acid alterations, in particular amino acid substitutions, insertions or deletions. Such proteases are, for example, developed by targeted genetic modification, i.e., by mutagenesis methods, and optimized for specific applications or with regard to specific properties (for example with regard to their catalytic activity or stability, etc.). Furthermore, nucleic acids can be introduced into recombination approaches and can thus be used to generate completely new types of proteases or other polypeptides. The aim is to introduce targeted mutations such as substitutions, insertions or deletions into the known molecules in order, for example, to improve the cleaning performance of enzymes. For this purpose, in particular the surface charges and/or the isoelectric point of the molecules and thus their interactions with the substrate can be modified. For instance, the net charge of the enzymes can be altered in order to influence the substrate binding, in particular for use in washing and cleaning agents. Alternatively or additionally, one or more corresponding mutations can increase the stability or catalytic activity of the enzyme and thus improve its cleaning performance. Advantageous properties of individual mutations, e.g., individual substitutions, can complement one another. A protease that has already been optimized with regard to certain properties can therefore be further developed, for example with regard to its stability towards surfactants and/or bleaching agents and/or other components.

A detergent contains the protease in an amount, in order of increasing preference, of from $1 \times 10^8$ to 5 wt. %, from 0.0001 to 1 wt. %, from 0.0005 to 0.5 wt. %, from 0.001 to 0.1 wt. %, in each case based on active protein and based on the total weight of the detergent.

In a further embodiment, the protease is characterized in that its cleaning performance (after storage, e.g., over 2 weeks) compared to conventional proteases and/or the wild-type enzyme (SEQ ID NO:1) and/or a corresponding already performance-enhanced starting variant (SEQ ID NO:2 from WO 2013/060621 A1) is not significantly reduced, i.e., has at least 80% of the reference washing performance, preferably at least 100%, more preferably at least 110% or more.

Within the context of the disclosure, cleaning performance is understood to mean the ability of an agent to partially or completely remove an existing stain, in particular the lightening performance on one or more stains on textiles. Examples of such stains are blood on cotton or chocolate milk/soot on cotton, cocoa on cotton or porridge on cotton. Within the context of the disclosure, both the detergent, which comprises the protease, or the washing liquor formed by this agent, and the protease itself have a cleaning performance. The cleaning performance of the protease thus contributes to the cleaning performance of the agent or the washing liquor formed by the agent. The cleaning performance is preferably ascertained as described hereafter.

Washing liquor is understood to mean the use solution containing the detergent, which solution acts on the textiles or fabrics and thus comes into contact with the stains present on the textiles or fabrics. The washing liquor is usually formed when the washing process begins and the detergent is diluted with water, for example in a washing machine or in another suitable container.

The cleaning performance can be determined in a washing system containing a detergent in a dosage between 2.0 and 8.0 grams per liter of washing liquor and the protease. The proteases to be compared are used in the same concentration (based on active protein). The activity-equivalent use of the relevant protease ensures that the respective enzymatic properties, for example the cleaning performance on certain stains, are compared even if the ratio of active substance to total protein (the values of the specific activity) diverges. In general, low specific activity can be compensated for by adding a larger amount of protein. Furthermore, the enzymes to be examined can also be used in the same amount of substance or amount by weight if the enzymes to be examined have a different affinity for the test substrate in an activity test. The expression "same amount of substance" in this context relates to a molar use of the enzymes to be examined. The expression "equal weight" relates to the use of the same weight of the enzymes to be examined.

The concentration of the protease in the detergent intended for this washing system is 0.0001 to 0.1 wt. %, preferably 0.001 to 0.1 wt. %, more preferably 0.01 to 0.06 wt. % and particularly preferably 0.001 to 0.02 wt. % based on active protein.

A preferred liquid detergent for such a washing system is composed as follows (all data in percent by weight): <1% anti-foam agent, 1-4% citric acid, 0.5-3% glycerol, 0.3-2% NaOH, 4-8% 1,2-propanediol, 2-5% FAEOS (fatty alcohol ether sulfate), 5-9% non-ionic surfactants (FAEO), 7-12% anionic surfactants (LAS), 0.5-1.5% protease stabilizer, 1-3% palm kernel oil fatty acids, 0.5-2% HEDP (1-hydroxyethane-(1,1-di-phosphonic acid)), 2-6% monoethanolamine (MEA), 0.2-1% soil release polymer, with the remainder being demineralized water. The dosage of the liquid detergent is preferably between 2.0 and 8.0 grams per liter of washing liquor, for example 2.5 g/L, 3.2 g/L, 3.5 g/L, 4.0 g/L, 4.7 g/L, 4.9 g/L, 5.5 g/L or 5.9 g/L wash liquor or approximately 55 g/job. Washing is preferably carried out in a pH range of from approximately 9 to approximately 12, preferably from approximately 10 to 11, particularly preferably at pH 10.

The degree of whiteness, i.e., the lightening of stains, as a measure of the cleaning performance is preferably determined by optical measuring methods, preferably photometrically. A suitable device for this purpose is for example the Minolta CM508d spectrometer. Usually, the devices used for the measurement are calibrated beforehand with a white standard, preferably a supplied white standard.

Methods for determining protease activity are well known to, and routinely used by, a person skilled in the art of enzyme technology. For example, such methods are disclosed in Tenside ["Surfactants"], vol. 7 (1970), pp. 125-132. Alternatively, the protease activity can be determined by the release of the chromophore para-nitroaniline (pNA) from the substrate suc-L-Ala-L-Ala-L-Pro-L-Phe-p-nitroanilide (AAPF). The protease cleaves the substrate and releases pNA. The release of the pNA causes an increase in absorbance at 410 nm, the temporal progression of which is a measure of the enzymatic activity (cf. Del Mar et al., 1979). The measurement is carried out at a temperature of 25° C., a pH of 8.6, and a wavelength of 410 nm. The measuring time is 5 min and the measuring interval is 20 s to 60 s. The protease activity is usually indicated in protease units (PE). Suitable protease activities amount to 2.25, 5 or 10 PE per mL of washing liquor, for example. However, the protease activity is not equal to zero.

An alternative test for establishing the proteolytic activity of the proteases is an optical measuring method, preferably a photometric method. The appropriate test involves the protease-dependent cleavage of the substrate protein casein. This is cleaved by the protease into a multitude of smaller partial products. The totality of these partial products has an increased absorption at 290 nm compared with uncleaved casein, it being possible for this increased absorption to be determined using a photometer, and thus for a conclusion to be drawn regarding the enzymatic activity of the protease.

The protein concentration can be determined using known methods, for example the BCA method (bicinchoninic acid; 2,2'-bichinolyl-4,4'-dicarboxylic acid) or the Biuret method (Gornall et al. (1948), J. Biol. Chem., 177:751-766). The active protein concentration can be determined in this regard by titrating the active centers using a suitable irreversible inhibitor and determining the residual activity (Bender et al., (1966), J. Am. Chem. Soc. 88(24):5890-5913).

Preferred embodiments of proteases achieve such advantageous cleaning performance even at low temperatures, in particular in the temperature ranges between 10 and 60° C., preferably between 15 and 50° C. and particularly preferably between 20 and 40° C.

A detergent is understood to be all conceivable types of detergent, both concentrates and undiluted agents, for use on a commercial scale, in washing machines or for hand washing or cleaning. These include, for example, detergents for textiles, carpets or natural fibers, for which the term detergent is used. Within the context of the disclosure, the detergents also include auxiliary detergents, which are added to the actual detergent when washing textiles manually or using a machine in order to achieve an additional effect. Furthermore, detergents also include textile pre-treatment and post-treatment agents, i.e., the agents with which the item of laundry is brought into contact before the actual washing cycle, for example to loosen stubborn stains, and also the agents which give the laundry further desirable properties such as a pleasant feel, crease resistance or low static charge in a step subsequent to the actual textile wash. The last-mentioned agents include fabric softeners, inter alia.

The detergents, which may be in the form of powdered or granular solids, in compacted or further-compacted particle form, homogeneous solutions or suspensions, may contain all known ingredients customary in such detergents in addition to a protease, with the detergent preferably containing such an additional ingredient in an amount of from 0.01 to 99.9 wt. %. The detergents can in particular contain surfactants, builders, polymers, glass corrosion inhibitors, corrosion inhibitors, bleaching agents such as peroxygen compounds, bleach activators or bleach catalysts. They may also contain water-miscible organic solvents, additional enzymes, enzyme stabilizers, sequestering agents, electrolytes, pH regulators and/or additional auxiliaries such as optical brighteners, graying inhibitors, dye transfer inhibitors, foam regulators, as well as dyes and fragrances, and combinations thereof.

In particular, anionic surfactants, non-ionic surfactants and mixtures thereof are suitable. The agents can contain one or more surfactants, with anionic surfactants, non-ionic surfactants and mixtures thereof being particularly suitable, but cationic, zwitterionic and/or amphoteric surfactants can also be contained. The agents preferably contain 5 to 70 wt. % surfactant, preferably 5 to 55 wt. % and more preferably 5 to 35 wt. % surfactant. The detergents particularly preferably contain not more than 30 wt. % surfactants, very particularly preferably not more than 20 wt. % surfactants.

Suitable anionic surfactants are in particular soaps and those containing sulfate or sulfonate groups preferably having alkali ions as cations. Usable soaps are preferably the alkali salts of saturated or unsaturated $C_{12-18}$ fatty acids. Fatty acids of this kind may also be used in a not completely neutralized form. Suitable sulfate-type surfactants include the salts of sulfuric acid half-esters of $C_{12-18}$ fatty alcohols atoms and the sulfation products of the mentioned non-ionic surfactants having a low degree of ethoxylation. Surfactants of the sulfonate type that can be used include, for example, $C_{9-14}$ alkylbenzene sulfonates, alkane sulfonates which are obtained from $C_{12-18}$ alkanes, for example by sulfochlorination or sulfoxidation with subsequent hydrolysis or neutralization, $C_{12-18}$ olefin sulfonates resulting from the reaction of corresponding monoolefins with sulfur trioxide, mixtures of alkene and hydroxyalkane sulfonates, disulfonates, such as those obtained from $C_{12-18}$ monoolefins with terminal or internal double bonds by sulfonation with gaseous sulfur trioxide and subsequent alkaline or acidic hydrolysis of the sulfonation products, and α-sulfofatty acid esters (ester sulfonates) resulting from the sulfonation of fatty acid methyl or ethyl esters, e.g., α-sulfonated methyl esters of hydrogenated coconut, palm kernel or tallow fatty acids.

The agent preferably has 2 to 55 wt. %, more preferably 3 to 35 wt. %, anionic surfactant; Very preferably, the agent contains 3 to 15 wt. % alkyl benzene sulfonate. In addition, the agent can preferably also contain other anionic surfactants, in particular alkyl ether sulfates, and non-ionic surfactants, in particular fatty alcohol alkoxylates. These can then make up the remainder of the surfactants.

Suitable alkylbenzene sulfonates are preferably selected from linear or branched alkylbenzene sulfonates of the formula

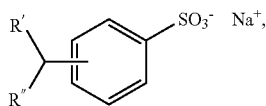

in which R' and R", independently, are H or alkyl, and together contain 6 to 19, preferably 7 to 15, and in particular 9 to 13, C atoms. A very particularly preferred representative is sodium dodecylbenzene sulfonate.

The alkali salts and in particular the sodium salts of the sulfuric acid half-esters of $C_{12-18}$ fatty alcohols, for example from coconut fatty alcohol, tallow fatty alcohol, lauryl alcohol, myristyl alcohol, cetyl alcohol or stearyl alcohol, or of $C_{10-20}$ oxo alcohols and the half-esters of secondary alcohols having these chain lengths are preferred as alk(en)yl sulfates. Alk(en)yl sulfates of the mentioned chain length that contain a synthetic straight-chain alkyl functional group prepared on a petrochemical basis and have a degradation behavior similar to that of the adequate compounds based on fat chemical raw materials are also preferred. From a washing perspective, the $C_{12-16}$ alkyl sulfates and $C_{12-15}$ alkyl sulfates and also $C_{14-15}$ alkyl sulfates are preferred.

Fatty alcohol ether sulfates, such as the sulfuric acid monoesters of straight-chain or branched $C_{7-21}$ alcohols ethoxylated with 1 to 6 mol ethylene oxide, such as 2-methyl-branched $C_{9-11}$ alcohols having, on average, 3.5 mol ethylene oxide (EO) or $C_{12-18}$ fatty alcohols having 1 to 4 EO, are also suitable.

Examples of suitable alkyl ether sulfates are compounds of the formula $R^1$—O-(AO)$_n$—SO$_3^-$X$^+$. In this formula, $R^1$ represents a linear or branched, substituted or unsubstituted alkyl functional group, preferably a linear, unsubstituted alkyl functional group, particularly preferably a fatty alcohol functional group. Preferred functional groups $R^1$ are selected from decyl, undecyl, dodecyl, tridecyl, tetradecyl, pentadecyl, hexadecyl, heptadecyl, octadecyl, nonadecyl and eicosyl functional groups and mixtures thereof, the representatives having an even number of C atoms being preferred. Particularly preferred functional groups $R^1$ are derived from $C_{12-18}$ fatty alcohols, e.g., from coconut fatty alcohol, tallow fatty alcohol, lauryl, myristyl, cetyl or stearyl alcohol, or from $C_{10-20}$ oxo alcohols. AO represents an ethylene oxide (EO) group or propylene oxide (PO) group, preferably an ethylene oxide group. The index n represents an integer from 1 to 50, preferably from 1 to 20, and in particular from 2 to 10. Very particularly preferably, n represents the numbers 2, 3, 4, 5, 6, 7 or 8. $X^+$ represents a monovalent cation or the nth part of an n-valent cation, the alkali metal ions, including Na$^+$ or K$^+$, being preferred in this case, with Na$^+$ being most preferred. Further cations X$^+$ can be selected from NH$_4^+$, ½ Zn$^{2+}$, ½ Mg$^{2+}$, ½ Ca$^{2+}$, ½ Mn$^{2+}$ and mixtures thereof.

In various embodiments, the alkyl ether sulfate can be selected from fatty alcohol ether sulfates of the formula

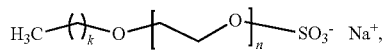

where k=11 to 19, and n=2, 3, 4, 5, 6, 7 or 8. Very particularly preferred representatives are Na—$C_{12-14}$ fatty alcohol ether sulfates having 2 EO (k=11-13, n=2). The degree of ethoxylation indicated represents a statistical average that can correspond to an integer or a fractional number for a specific product. The degrees of alkoxylation specified represent statistical averages that can correspond to an integer or a fractional number for a specific product. Preferred alkoxylates/ethoxylates have a narrowed homolog distribution (narrow range ethoxylates, NRE).

It has proven advantageous for cold-wash performance if the detergents additionally contain soap(s) as the anionic surfactant. Preferred detergents are therefore characterized in that they contain soap(s). Saturated fatty acid soaps are suitable, such as the salts of lauric acid, myristic acid, palmitic acid, stearic acid, hydrogenated erucic acid and behenic acid, and in particular soap mixtures derived from natural fatty acids, such as coconut fatty acids, palm kernel fatty acids or tallow fatty acids.

Suitable non-ionic surfactants are in particular alkyl glycosides and ethoxylation and/or propoxylation products of alkyl glycosides or linear or branched alcohols each having 8 to approximately 18 C atoms in the alkyl portion and 3 to 20, preferably 4 to 10, alkyl ether groups. Corresponding ethoxylation and/or propoxylation products of N-alkyl amines, vicinal diols, fatty acid esters and fatty acid amides which, with regard to the alkyl portion, correspond to the long-chain alcohol derivatives mentioned, and of alkyl phenols having 5 to 12 C atoms in the alkyl functional group are also suitable.

Non-ionic surfactants that are preferably used are alkoxylated, advantageously ethoxylated, in particular primary alcohols having preferably 8 to 18 C atoms and, on average, 1 to 12 mols of ethylene oxide (EO) per mol of alcohol, in which the alcohol functional group can be linear or preferably methyl-branched in position 2, or can contain linear and methyl-branched functional groups in admixture, as are usually present in oxo alcohol functional groups. However, alcohol ethoxylates having linear functional groups of alcohols of native origin having 12 to 18 C atoms, for example of coconut, palm, tallow fatty or oleyl alcohol, and an average of 2 to 8 EO per mol of alcohol, are particularly preferred. Preferred ethoxylated alcohols include, e.g., $C_{12-14}$ alcohols having 3 EO or 4 EO, $C_{9-11}$ alcohols having 7 EO, $C_{13-15}$ alcohols having 3 EO, 5 EO, 7 EO or 8 EO, $C_{12-18}$ alcohols having 3 EO, 5 EO or 7 EO, and mixtures thereof, such as mixtures of $C_{12}$-14 alcohol having 3 EO and $C_{12-18}$ alcohol having 5 EO. The degrees of ethoxylation indicated represent statistical averages that can correspond to an integer or a fractional number for a specific product. Preferred alcohol ethoxylates have a narrowed homolog distribution (narrow range ethoxylates, NRE). In addition to these non-ionic surfactants, fatty alcohols having more than 12 EO can also be used. Examples of these are tallow fatty alcohols having 14 EO, 25 EO, 30 EO, or 40 EO.

Another class of non-ionic surfactants that are preferably used, which are used either as the sole non-ionic surfactant or in combination with other non-ionic surfactants, is alkoxylated, preferably ethoxylated or ethoxylated and propoxylated fatty acid alkyl esters, preferably having 1 to 4 carbon atoms in the alkyl chain, in particular fatty acid methyl esters.

Another class of non-ionic surfactants that can advantageously be used is the alkyl polyglycosides (APG). Alkyl polyglycosides that can be used have the general formula RO(G)$_z$, in which R represents a linear or branched, in particular methyl-branched at the 2-position, saturated or unsaturated aliphatic functional group having 8 to 22, preferably 12 to 18, C atoms, and G is the symbol that represents a glycose unit having 5 or 6 C atoms, preferably glucose. The degree of glycosidation z is between 1.0 and 4.0, preferably between 1.0 and 2.0, and in particular between 1.1 and 1.4. Linear alkyl polyglycosides are preferably used, which is to say alkyl polyglycosides in which the polyglycol functional group is a glucose functional group and the alkyl functional group is an n-alkyl functional group.

Non-ionic surfactants of the aminoxide type, for example N-cocoalkyl-N,N-dimethylamine oxide and N-tallow-alkyl-N,N-dihydroxyethylamine oxide, and of the fatty acid alkanolamides may also be suitable. The quantity of these non-ionic surfactants is preferably no more than that of the ethoxylated fatty alcohols, in particular no more than half thereof.

Non-ionic surfactants that can preferably be used in the detergent have the formula $R^1$—$CH(OH)CH_2O$-$(AO)_w$-$(A'O)_x$-$(A''O)_y$-$(A'''O)_z$—$R^2$, in which $R^1$ represents a straight-chain or branched, saturated or mono- or polyunsaturated $C_{6-24}$ alkyl or alkenyl functional group; $R^2$ represents a linear or branched hydrocarbon functional group having 2 to 26 carbon atoms; A, A', A''' and A'''' represent, independently of one another, a functional group from the group —$CH_2CH_2$—, —$CH_2CH_2$—$CH_2$—, —$CH_2$—$CH(CH_3)$—, —$CH_2$—$CH_2$—$CH_2$—$CH_2$—, —$CH_2$—$CH(CH_3)$—$CH_2$—, —$CH_2$—$CH(CH_2$—$CH_3)$, and w, x, y and z represent values between 0.5 and 120, where x, y and/or z can also be 0. By adding the above-mentioned non-ionic surfactants of the formula $R^1$—$CH(OH)CH_2O$-$(AO)w$-$(A'O)x$-$(A''O)_y$-$(A'''O)_z$—$R^2$, subsequently also referred to as "hydroxy mixed ethers," the cleaning performance of enzyme-containing preparations can be significantly improved, both in comparison with surfactant-free systems and in comparison with systems containing alternative non-ionic surfactants, for example from the group of polyalkoxylated fatty alcohols.

By using these non-ionic surfactants having one or more free hydroxyl group(s) on one or both terminal alkyl groups, the stability of the enzymes contained in the detergent preparations can be improved significantly.

Particularly preferred are end-capped poly(oxyalkylated) non-ionic surfactants which, according to the formula $R^1O$[$CH_2CH_2O$]$xCH_2CH(OH)R^2$, also comprise, in addition to a functional group $R^1$, which represents linear or branched, saturated or unsaturated, aliphatic or aromatic hydrocarbon functional groups having 2 to 30 carbon atoms, preferably having 4 to 22 carbon atoms, a linear or branched, saturated or unsaturated, aliphatic or aromatic hydrocarbon functional group $R^2$ having 1 to 30 carbon atoms, where x represents values between 1 and 90, preferably values between 30 and 80, and in particular values between 30 and 60.

Surfactants of the formula $R^1O$[$CH_2CH(CH_3)O$]$_x$[$CH_2CH_2O$]$_y$$CH_2CH(OH)R^2$ are particularly preferred, in which $R^1$ represents a linear or branched aliphatic hydrocarbon functional group having 4 to 18 carbon atoms or mixtures thereof, $R^2$ denotes a linear or branched hydrocarbon functional group having 2 to 26 carbon atoms or mixtures thereof, x represents values between 0.5 and 1.5, and y represents a value of at least 15. The group of these non-ionic surfactants includes, for example, the $C_{2-26}$ fatty alcohol-$(PO)_1$-$(EO)_{15-40}$-2-hydroxyalkyl ethers, in particular including the $C_{8-10}$ fatty alcohol-$(PO)_1$-$(EO)_{22}$-2-hydroxydecyl ethers.

Particularly preferred are also end-capped poly(oxyalkylated) non-ionic surfactants of the formula $R^1O$[$CH_2CH_2O$]$_x$[$CH_2CH(R^3)O$]$_y$$CH_2CH(OH)R^2$, in which $R^1$ and $R^2$ represent, independently of one another, a linear or branched, saturated or mono- or polyunsaturated hydrocarbon functional group having 2 to 26 carbon atoms, $R^3$ is selected, independently of one another, from —$CH_3$, —$CH_2CH_3$, —$CH_2CH_2$—$CH_3$, —$CH(CH_3)_2$, but preferably represents —$CH_3$, and x and y represent, independently of one another, values between 1 and 32, with non-ionic surfactants where $R^3$=—$CH_3$ and values for x of from 15 to 32 and for y of 0.5 and 1.5 being very particularly preferred.

Further non-ionic surfactants that can preferably be used are the end-capped poly(oxyalkylated) non-ionic surfactants of the formula $R^1O$[$CH_2CH(R^3)O$]$_x$[$CH_2$]$_k$$CH(OH)$[$CH_2$]$_j$$OR^2$, in which $R^1$ and $R^2$ represent linear or branched, saturated or unsaturated, aliphatic or aromatic hydrocarbon functional groups having 1 to 30 carbon atoms, $R^3$ represents H or a methyl, ethyl, n-propyl, iso-propyl, n-butyl, 2-butyl or 2-methyl-2-butyl functional group, x represents values between 1 and 30, and k and j represent values between 1 and 12, preferably between 1 and 5. If the value x is 2, each $R^3$ in the above formula $R^1O$[$CH_2CH(R^3)O$]$_x$[$CH_2$]$_k$$CH(OH)$[$CH_2$]$_j$$OR^2$ can be different. $R^1$ and $R^2$ are preferably linear or branched, saturated or unsaturated, aliphatic or aromatic hydrocarbon functional groups having 6 to 22 carbon atoms, with functional groups having 8 to 18 C atoms being particularly preferred. For the functional group $R^3$, H, —$CH_3$ or —$CH_2CH_3$ are particularly preferred. Particularly preferred values for x are in the range of from 1 to 20, in particular from 6 to 15. As described above, each $R^3$ in the above formula can be different if x≥2. In this way, the alkylene oxide unit in square brackets can be varied. For example, if x represents 3, the functional group $R^3$ can be selected in order to form ethylene oxide ($R^3$=H) or propylene oxide ($R^3$=$CH_3$) units, which can be joined together in any sequence, for example (EO)(PO)(EO), (EO)(EO)(PO), (EO)(EO)(EO), (PO)(EO)(PO), (PO)(PO)(EO) and (PO)(PO)(PO). The value 3 for x has been selected here as an example and can by all means be greater, the range of variation increasing as the values for x increase and including a large number of (EO) groups combined with a small number of (PO) groups, or vice versa. Particularly preferred end-capped poly(oxyalkylated) alcohols of the above formula have values of k=1 and j=1, and therefore the previous formula is simplified to $R^1O$[$CH_2CH(R^3)O$]$_x$$CH_2CH(OH)$$CH_2OR^2$. In the last-mentioned formula, $R^1$, $R^2$ and $R^3$ are as defined above and x represents numbers from 1 to 30, preferably 1 to 20, and in particular 6 to 18. Surfactants in which the functional groups $R^1$ and $R^2$ have 9 to 14 C atoms, $R^3$ represents H, and x assumes values from 6 to 15 are particularly preferred.

Finally, the non-ionic surfactants of the general formula $R^1$—$CH(OH)CH_2O$-$(AO)_w$—$R^2$ have proven to be particularly effective, where $R^1$ represents a straight-chain or branched, saturated or mono- or polyunsaturated $C_{6-24}$ alkyl or alkenyl functional group; $R^2$ represents a linear or branched hydrocarbon functional group having 2 to 26 carbon atoms; A represents a functional group from the group —$CH_2CH_2$—, —$CH_2CH_2$—$CH_2$—, —$CH_2$—$CH(CH_3)$—, and w represents values between 1 and 120, preferably 10 to 80, in particular 20 to 40. The group of these non-ionic surfactants includes, for example, $C_{4-22}$ fatty alcohol-$(EO)_{10-80}$-2-hydroxyalkyl ethers, in particular also $C_{8-12}$ fatty alcohol-$(EO)_{22}$-2-hydroxydecyl ethers and $C_{4-22}$ fatty alcohol-$(EO)_{40-80}$-2-hydroxyalkyl ethers.

Preferred detergents are characterized in that the detergent contains at least one non-ionic surfactant, preferably a non-ionic surfactant from the group of hydroxy mixed ethers, the proportion by weight of the non-ionic surfactant with respect to the total weight of the detergent preferably being 0.2 to 20 wt. %, preferably 1 to 18 wt. %, more preferably 2 to 15 wt. % and particularly preferably 5 to 10 wt. %.

Suitable amphoteric surfactants are, for example, betaines of the formula $(R^{iii})(R^{iv})(R^v)N^+CH_2COO^-$, in which $R^{iii}$ denotes an alkyl group, which is optionally interrupted by heteroatoms or heteroatom groups, having 8 to 25, preferably 10 to 21, carbon atoms, and $R^{iv}$ and $R^v$ denote identical or different alkyl groups having 1 to 3 carbon atoms, in particular $C_{10-18}$ alkyl dimethyl carboxymethyl betaine and $C_{11-17}$ alkyl amidopropyl dimethyl carboxymethyl betaine.

Suitable cationic surfactants are, inter alia, the quaternary ammonium compounds of the formula $(R^{vi})(R^{vii})(R^{viii})(R^{ix})N^+X^-$, in which $R^{vi}$ to $R^{ix}$ are four identical or different, in particular two long-chain and two short-chain, alkyl groups, and $X^-$ is an anion, in particular a halide ion, e.g., didecyl dimethyl ammonium chloride, alkyl benzyl didecyl ammonium chloride and mixtures thereof. Further suitable cationic surfactants are the quaternary surface-active compounds, in particular having a sulfonium, phosphonium, iodonium or arsonium group, which are also known as antimicrobial active ingredients. By using quaternary surface-active compounds having an antimicrobial effect, the agent can be provided with an antimicrobial effect or the antimicrobial effect that may already be present due to other ingredients can be improved.

Complexing agents are another preferred component of detergents. Particularly preferred complexing agents are the phosphonates, provided that their use is permitted by regulations. In addition to 1-hydroxyethane-1,1-diphosphonic acid, the complexing phosphonates include a number of different compounds such as diethylenetriamine penta(methylene phosphonic acid) (DTPMP). Hydroxy alkane or amino alkane phosphonates are particularly preferred in this application. Among the hydroxy alkane phosphonates, 1-hydroxyethane-1,1-diphosphonate (HEDP) has particular significance as a cobuilder. It is preferably used as a sodium salt, the disodium salt reacting in a neutral manner and the tetrasodium salt reacting in an alkaline manner (pH 9). Possible preferable aminoalkane phosphonates include ethylenediamine tetramethylene phosphonate (EDTMP), diethylenetriamine pentamethylene phosphonate (DTPMP) and the higher homologs thereof. They are preferably used in the form of the neutrally reacting sodium salt, for example as the hexasodium salt of EDTMP or as the hepta- and octa-sodium salt of DTPMP. Of the class of phosphonates, HEDP is preferably used as a builder. The aminoalkane phosphonates additionally have a pronounced capability to bind heavy metals. Accordingly, it may be preferred, in particular if the agents also contain bleach, to use aminoalkane phosphonates, in particular DTPMP, or to use mixtures of the mentioned phosphonates. A detergent which is preferred within the context of this application contains one or more phosphonate(s) from the group amino trimethylene phosphonic acid (ATMP) and/or salts thereof; ethylenediamine tetra(methylene phosphonic acid) (EDTMP) and/or the salts thereof; diethylenetriamine penta(methylene phosphonic acid) (DTPMP) and/or the salts thereof; 1-hydroxyethane-1,1-diphosphonic acid (HEDP) and/or the salts thereof; 2-phosphonobutane-1,2,4-tricarboxylic acid (PBTC) and/or the salts thereof; hexamethylenediamine tetra(methylene phosphonic acid) (HDTMP) and/or the salts thereof; and nitrilotri(methylenephosphonic acid) (NTMP) and/or the salts thereof. Detergents which contain 1-hydroxyethane-1,1-diphosphonic acid (HEDP) or diethylenetriaminepenta (methylenephosphonic acid) (DTPMP) as phosphonates are particularly preferred. The detergents may, of course, contain two or more different phosphonates. Detergents that are preferred are characterized in that the detergent contains at least one complexing agent from the group of phosphonates, preferably 1-hydroxyethane-1,1-diphosphonate, the proportion by weight of the phosphonate with respect to the total weight of the detergent preferably being between 0.1 and 8.0 wt. %, more preferably 0.2 and 5.0 wt. %, even more preferably 0.3 and 3.0 wt. % and particularly preferably 0.5-2.0 wt. %.

The detergents also preferably contain builders, preferably at least one water-soluble and/or water-insoluble, organic and/or inorganic builder. The builders include in particular the silicates, carbonates and/organic cobuilders.

Polycarboxylates/polycarboxylic acids, polymeric polycarboxylates, aspartic acid, polyacetals, dextrins, other organic cobuilders and phosphonates are particularly noteworthy as organic cobuilders. These classes of substances are described below. Organic cobuilder substances of this kind can, if desired, be contained in amounts of up to 40 wt. %, in particular up to 25 wt. %, and preferably from 1 to 8 wt. %.

Suitable organic builder substances are, for example, the polycarboxylic acids that can be used in the form of the free acids and/or the sodium salts thereof, where polycarboxylic acids are understood to mean the carboxylic acids which carry more than one acid function. For example, these are citric acid, adipic acid, succinic acid, glutaric acid, malic acid, tartaric acid, maleic acid, fumaric acid, saccharic acid, carboxylmethylinulin, monomeric and polymeric am inopolycarboxylic acids, in particular glycinediacetic acid, methylglycinediacetic acid, glutaminediacetic acid, nitrilotriacetic acid (NTA), iminodisuccinates such as ethylenediamine-N,N'-disuccinic acid and hydroxyiminodisuccinate, ethylenediaminetetraacetic acid and polyaspartic acid, polyphosphonic acids, in particular aminotris(methylenephosphonic acid), ethylenediamine tetrakis (methylenephosphonic acid), lysine tetra(methylenephosphonic acid) and 1-hydroxyethane-1,1-diphosphonic acid, polymeric hydroxy compounds such as dextrin, and polymeric (poly)carboxylic acids, polycarboxylates which can be obtained in particular by oxidizing polysaccharides or dextrins, and/or polymeric acrylic acids, methacrylic acids, maleic acids, and mixed polymers thereof, which may also contain, polymerized therein, small proportions of polymerizable substances, without a carboxylic acid functionality. Organic builder substances of this kind can, if desired, be contained in amounts of up to 50 wt. %, in particular up to 25 wt. %, preferably of from 10 to 20 wt. % and particularly preferably from 1 to 5 wt. %.

In addition to their builder effect, the free acids typically also have the property of being an acidification component and are thus also used for setting a lower and milder pH of detergents. Particularly noteworthy here are citric acid, succinic acid, glutaric acid, adipic acid, gluconic acid, and any mixtures thereof. Citric acid or salts of citric acid are particularly preferably used as builder substances. Further particularly preferred builder substances are selected from methylglycinediacetic acid (MGDA), glutamic acid diacetate (GLDA), aspartic acid diacetate (ASDA), hydroxyethyl-iminodiacetate (HEIDA), iminodisuccinate (IDS), ethylenediamine disuccinate (EDDS), carboxymethyl inulin and polyaspartate.

In preferred embodiments, citric acid and/or citrate is used as the water-soluble, organic builder. It is particularly preferred to use 0.5 to 25 wt. %, preferably 0.75 to 12.5 wt. %, more preferably 1 to 4 wt. %, citric acid and/or 0.5 to 25 wt. %, preferably 0.75 to 12.5 wt. %, more preferably 1 to 4 wt. %, citrate, preferably alkali citrate, more preferably sodium citrate. Citric acid/citrate can each be used in the form of their hydrates, for example citric acid can be used in the form of the monohydrate, and citrate can be used in the form of the trisodium citrate dihydrate.

Polymeric polycarboxylates are also suitable as builders. These are, for example, the alkali metal salts of polyacrylic acid or polymethacrylic acid, for example those having a relative molecular mass of from 500 to 70,000 g/mol. For the purpose of this application, the molar masses indicated for polymeric polycarboxylates are weight-average molar masses $M_w$ of the particular acid form which have been determined in principle using gel permeation chromatography (GPC), a UV detector having been used. The measurement was carried out against an external polyacrylic acid standard which, owing to the structural relationship thereof with the tested polymers, yields realistic molecular weight values. These specifications differ significantly from the molecular weight specifications for which polystyrene sulfonic acids are used as the standard. The molar masses measured against polystyrene sulfonic acids are generally considerably higher than the molar masses indicated in this application. Suitable polymers are in particular polyacrylates which preferably have a molecular mass of from 2,000 to 20,000 g/mol. Due to their superior solubility, short-chain polyacrylates having molar masses of from 2,000 to 10,000 g/mol, and particularly preferably from 3,000 to 5,000 g/mol, may in turn be preferred from this group. In addition, copolymeric polycarboxylates are suitable, in particular those of acrylic acid with methacrylic acid and of acrylic acid or methacrylic acid with maleic acid. Copolymers of acrylic acid with maleic acid which contain 50 wt. % to 90 wt. % of acrylic acid and 50 wt. % to 10 wt. % of maleic acid have been found to be particularly suitable. The relative molecular mass thereof, based on free acids, is generally 2,000 to 70,000 g/mol, preferably 20,000 to 50,000 g/mol, and in particular 30,000 to 40,000 g/mol.

A solid agent preferably contains at least one water-soluble and/or water-insoluble, organic and/or inorganic builder. The water-soluble organic builder substances include the above-mentioned organic builder substances. In addition to the water-soluble organic builders mentioned above, the agents may also further contain inorganic water-soluble builders. In particular, alkali silicates, alkali carbonates, alkali hydrogen carbonates, alkali phosphates and/or sesquicarbonates, which can be present in the form of their alkaline, neutral, or acidic sodium or potassium salts, can be used as water-soluble inorganic builder materials. Small amounts of calcium carbonate may optionally also be contained in solid textile detergents. Water-soluble crystalline and/or amorphous alkali silicates are suitable, for example. The alkali silicates that are suitable in the agents as builders preferably have a molar ratio of alkali oxide to $SiO_2$ of less than 0.95, in particular of from 1:1.1 to 1:12, and may be present in amorphous or crystalline form. Preferred alkali silicates are sodium silicates, in particular amorphous sodium silicates, having a molar ratio $Na_2O:SiO_2$ of from 1:2 to 1:2.8. Crystalline phyllosilicates of the general formula $Na_2Si_xO_{2x+1} \cdot y\ H_2O$, in which x, referred to as the module, is a number from 1.9 to 22, in particular 1.9 to 4, and y is a number from 0 to 33, and preferred values for x are 2, 3 or 4, are preferably used as crystalline silicates, which may be present alone or in a mixture with amorphous silicates. Preferred crystalline phyllosilicates are those in which x in the stated general formula assumes the values 2 or 3. Both β- and δ-sodium disilicates ($Na_2Si_2O_5 \cdot y\ H_2O$) are particularly preferred. Practically water-free crystalline alkali silicates of the above general formula, in which x is a number from 1.9 to 2.1 and which are produced from amorphous alkali silicates, may also be used in agents. In a further embodiment of agents, a crystalline sodium phyllosilicate having a module of from 2 to 3, as can be prepared from sand and soda, is used. Crystalline sodium silicates having a module in the range of from 1.9 to 3.5 are used in a further embodiment of agents. In agents containing amorphous as well as crystalline alkali silicates, the weight ratio of amorphous alkali silicate to crystalline alkali silicate is preferably 1:2 to 2:1 and in particular 1:1 to 2:1. Crystalline phyllosilicates of the above formula (1) are sold by Clariant GmbH under the trade name Na-SKS, for example Na-SKS-1 ($Na_2Si_{22}O_{45} \cdot x\ H_2O$, kenyaite), Na-SKS-2 ($Na_2Si_{14}O_{29} \cdot x\ H_2O$, magadiite), Na-SKS-3 ($Na_2Si_8O_{17} \cdot x\ H_2O$) or Na-SKS-4 ($Na_2Si_4O_9 \cdot x\ H_2O$, macatite). Of these, Na-SKS-5 (α-$Na_2Si_2O_5$), Na-SKS-7 (δ-$Na_2Si_2O_5$, natrosilite), Na-SKS-9 ($NaHSi_2O_5 \cdot 3H_2O$), Na-SKS-10 ($NaHSi_2O_5 \cdot 3H_2O$, kanemite), Na-SKS-11 (t-$Na_2Si_2O_5$) and Na-SKS-13 ($NaHSi_2O_5$), but in particular Na-SKS-6 (5-$Na_2Si_2O_5$), are especially suitable. In one embodiment of agents, a granular compound made of crystalline phyllosilicate and citrate, crystalline phyllosilicate and the above-described (co)polymeric polycarboxylic acid, or alkali silicate and alkali carbonate is used, as is commercially available under the name Nabion® 15, for example. Water-soluble inorganic builder materials of this kind are contained in agents preferably in amounts of from 1 to 20 wt. %, in particular 5 to 15 wt. %. Also of significance as water-soluble inorganic builder substances are the carbonates (and hydrogen carbonates), in particular sodium carbonate, and the phosphonic acids/phosphonates. Phosphonic acids are also understood as meaning optionally substituted alkyl phosphonic acids which can also have a plurality of phosphonic acid groups (so-called polyphosphonic acids). They are preferably selected from the hydroxy and/or aminoalkylphosphonic acids and/or their alkali salts, such as dimethylaminomethanediphosphonic acid, 3-aminopropane-1-hydroxy-1,1-diphosphonic acid, 1-amino-1-phenylmethanediphosphonic acid, 1-hydroxyethane-1,1-diphosphonic acid (HEDP), aminotris(methylenephosphonic acid), N,N,N',N'-ethylenediaminetetrakis(methylenephosphonic acid), diethylenetriaminepenta(methylenephosphonic acid) (DTPMP) and acylated derivatives of phosphorous acid, which can also be used in any mixtures.

In various embodiments, the builder system is preferably composed of the following components, in each case based on the total mass of the agent:
a) 0 to 10 wt. %, preferably 1 to 4 wt. % citric acid; and/or
b) 0 to 10 wt. %, preferably 1 to 4 wt. % citrate, preferably alkaline citrate; and/or
c) 0 to 40 wt. %, preferably 0 to 15 wt. %, particularly preferably 1 to 3 wt. %, alkali carbonate, which can also be replaced at least in part by alkali hydrogen carbonate, in particular sodium carbonate; and/or
d) 0 to 20 wt. %, preferably 3 to 10 wt. %, alkali silicate;
e) 0 to 10 wt. %, preferably 0.02 to 2 wt. %, particularly preferably 0.5 to 2 wt. %, phosphonic acid and/or alkali phosphonate, in particular HEDP and/or DTPMP; and/or
f) 0 to 10 wt. %, preferably 0.5 to 3 wt. %, polymeric polycarboxylate, in particular polyacrylate.

With regard to component f), for example, the alkali metal salts of polyacrylic acid or polymethacrylic acid are suitable, for example those with a relative molecular weight of from 500 to 70,000 g/mol. This substance class has already been described in detail above. The (co)polymeric polycarboxylates may be used either as a powder or as an aqueous solution.

The agents are preferably free of phosphate builders, i.e., they contain less than 1 wt. %, preferably no phosphate builders added intentionally.

The agents can also contain water-insoluble builder substances. Crystalline or amorphous water-dispersible alkali aluminosilicates, in amounts of up to 50 wt. %, preferably not more than 40 wt. %, in particular of from 3 to 20 wt. % and particularly preferably from 1 to 15 wt. %, are used in particular as water-insoluble inorganic builder materials. Among these, the crystalline sodium aluminosilicates in detergent quality, in particular zeolite A, zeolite P, zeolite MAP and optionally zeolite X, either alone or in mixtures, for example in the form of a co-crystallizate of the zeolites A and X (Vegobond® AX, a commercial product from Condea Augusta S.p.A.), are preferred. Amounts close to the stated upper limit are preferably used in solid particulate agents. Suitable aluminosilicates have in particular no particles having a particle size greater than 30 μm and preferably comprise at least 80 wt. % of particles having a size smaller than 10 μm. The calcium binding capacity, which can be determined according to DE 2412837 A1, of said aluminosilicates is generally in the range of from 100 to 200 mg CaO per gram.

In addition to the previously described builders, polymers having a cleaning action can be contained in the detergent. The proportion by weight of the polymers with respect to the total weight of detergents is preferably 0.1 to 20 wt. %, more preferably 1.0 to 15 wt. % and even more preferably 2.0 to 12 wt. %. Polymers containing sulfonic acid groups, in particular from the group of copolymeric polysulfonates, are preferably used as polymers having a cleaning action. These copolymeric polysulfonates contain, in addition to sulfonic acid group-containing monomer(s), at least one monomer from the group of unsaturated carboxylic acids. As the unsaturated carboxylic acid(s), unsaturated carboxylic acids of the formula $R^1(R^2)C=C(R^3)COOH$ are particularly preferably used, in which $R^1$ to $R^3$, independently of one another, represent —H, —$CH_3$, a straight-chain or branched saturated alkyl functional group having 2 to 12 carbon atoms, a straight-chain or branched, mono- or polyunsaturated alkenyl functional group having 2 to 12 carbon atoms, —$NH_2$—, —OH—, or —COOH-substituted alkyl or alkenyl functional groups as defined above, or represent —COOH or —$COOR^4$, where $R^4$ is a saturated or unsaturated, straight-chain or branched hydrocarbon functional group having 1 to 12 carbon atoms. Particularly preferred unsaturated carboxylic acids are acrylic acid, methacrylic acid, ethacrylic acid, α-chloroacrylic acid, α-cyanoacrylic acid, crotonic acid, α-phenylacrylic acid, maleic acid, maleic anhydride, fumaric acid, itaconic acid, citraconic acid, methylene malonic acid, sorbic acid, cinnamic acid, or mixtures thereof. Unsaturated dicarboxylic acids can of course also be used. For sulfonic acid group-containing monomers, those of the formula $R^5(R^6)C=C(R^7)—X—SO_3H$ are preferred, in which $R^5$ to $R^7$, independently of one another, represent —H, —$CH_3$, a straight-chain or branched saturated alkyl functional group having 2 to 12 carbon atoms, a straight-chain or branched, mono- or polyunsaturated alkenyl functional group having 2 to 12 carbon atoms, —$NH_2$—, —OH—, or —COOH-substituted alkyl or alkenyl functional groups, or represent —COOH or —$COOR^4$, where $R^4$ is a saturated or unsaturated, straight-chain or branched hydrocarbon functional group having 1 to 12 carbon atoms, and X represents an optionally present spacer group that is selected from —$(CH_2)_n$—, where n=0 to 4, —COO—$(CH_2)_k$—, where k=1 to 6, —C(O)—NH—C$(CH_3)_2$—, —C(O)—NH—C$(CH_3)_2$—$CH_2$— and —C(O)—NH—CH(CH$_2$CH$_3$)—CH$_2$—. Among these monomers, those of the formulas $H_2C=CH—X—SO_3H$, $H_2C=C(CH_3)—X—SO_3H$ and $HO_3S—X—(R^6)C=C(R^7)—X—SO_3H$ are preferred, in which $R^6$ and $R^7$, independently of one another, are selected from —H, —$CH_3$, —$CH_2CH_3$, —$CH_2CH_2CH_3$ and —$CH(CH_3)_2$, and X represents an optionally present spacer group that is selected from —$(CH_2)_n$—, where n=0 to 4, —COO—$(CH_2)_k$—, where k=1 to 6, —C(O)—NH—C$(CH_3)_2$—, —C(O)—NH—C$(CH_3)_2$—$CH_2$— and —C(O)—NH—CH(CH$_2$CH$_3$)—. Particularly preferred sulfonic acid group-containing monomers are 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxy-propanesulfonic acid, allyl sulfonic acid, methallyl sulfonic acid, allyloxybenzene sulfonic acid, methallyloxybenzene sulfonic acid, 2-hydroxy-3-(2-propenyloxy)propanesulfonic acid, 2-methyl-2-propene-1-sulfonic acid, styrene sulfonic acid, vinylsulfonic acid, 3-sulfopropylacrylate, 3-sulfopropylmethacrylate, sulfomethacrylamide, sulfomethylmethacrylamide, as well as mixtures of the above acids or water-soluble salts thereof. In the polymers, the sulfonic acid groups can be present entirely or partly in neutralized form. The use of partially or fully neutralized sulfonic acid groups copolymers containing sulfonic acid groups is preferred. The molar mass of the sulfo-copolymers that are preferably used can be varied in order to adapt the properties of the polymers to the desired intended use. As the non-ionic monomers, monomers of the formula $R^1(R^2)C=C(R^3)—X—R^4$ are preferably used, in which $R^1$ to $R^3$ represent, independently of one another, —H, —$CH_3$ or —$C_2H_5$, X represents an optionally present spacer group selected from —$CH_2$—, —C(O)O— and —C(O)—NH—, and $R^4$ represents a straight-chain or branched saturated alkyl functional group having 2 to 22 carbon atoms or an unsaturated, preferably aromatic functional group having 6 to 22 carbon atoms. Particularly preferred non-ionic monomers are butene, isobutene, pentene, 3-methylbutene, 2-methylbutene, cyclopentene, hexene, hexene-1,2-methlypentene-1, 3-methlypentene-1, cyclohexene, methylcyclopentene, cycloheptene, methylcyclohexene, 2,4,4-trimethylpentene-1,2,4,4-trimethylpentene-2,2,3-dimethylhexene-1,2,4-dimethylhexene-1,2,5-dimethylhexene-1,3,5-dimethylhexene-1,4,4-dimethylhexane-1, ethylcyclohexene, 1-octene, α-olefins having 10 or more carbon atoms such as 1-decene, 1-dodecene, 1-hexadecene, 1-octadecene and $C_{22}$ α-olefin, 2-styrene, α-methylstyrene, 3-methylstyrene, 4-propylstyrene, 4-cyclohexylstyrene, 4-dodecylstyrene, 2-ethyl-4-benzylstyrene, 1-vinyl naphthalene, 2-vinyl naphthalene, acrylic acid methyl ester, acrylic acid ethyl ester, acrylic acid propyl ester, acrylic acid butyl ester, acrylic acid pentyl ester, acrylic acid hexyl ester, methacrylic acid methyl ester, N-(methyl)acrylamide, acrylic acid-2-ethylhexyl ester, methacrylic acid-2-ethylhexyl ester, N-(2-ethylhexyl)acrylamide, acrylic acid octyl ester, methacrylic acid octyl ester, N-(octyl)acrylamide, acrylic acid lauryl ester, methacrylic acid lauryl ester, N-(lauryl)acrylamide, acrylic acid stearyl ester, methacrylic acid stearyl ester, N-(stearyl)acrylamide, acrylic acid behenyl ester, methacrylic acid behenyl ester and N-(behenyl)acrylamide, or mixtures thereof. The proportion by weight of the sulfonic-acid-group-containing copolymers with respect to the total weight of detergents is preferably 0.1 to 15 wt. %, more preferably 1.0 to 12 wt. % and even more preferably 2.0 to 10 wt. %.

In one embodiment, a detergent comprises,
5 to 70 wt. %, in particular 5 to 30 wt. %, surfactants and/or
0 to 10 wt. %, in particular 1 to 3 wt. %, water-soluble or water-dispersible inorganic builder material and/or
0 to 10 wt. %, and in particular 1 to 4 wt. %, water-soluble organic builder substances and/or
0.01 to 5 wt. % complexing agents and/or
0.01 to 5 wt. % graying inhibitor and/or
0.01 to 5 wt. % foam inhibitor, and/or
0.01 to 5 wt. % optical brighteners.

In a preferred embodiment, a liquid detergent comprises,
5 to 20 wt. %, in particular 9 to 17 wt. %, anionic surfactants and/or
1 to 20 wt. %, in particular 5 to 9 wt. %, non-ionic surfactants and/or
0.5 to 10 wt. %, in particular 1 to 4 wt. %, water-soluble organic builder substances, in particular citric acid or citrate, and/or
0.01 to 5 wt. %, in particular 0.5 to 2 wt. %, complexing agents, in particular HEDP, and/or
0.01 to 5 wt. %, in particular 0.2 to 1 wt. %, graying inhibitor and/or
0.01 to 5 wt. % foam inhibitor.

In a further preferred embodiment, a liquid detergent comprises
0 to 10 wt. %, in particular 1 to 3 wt. %, anionic surfactants and/or
5 to 20 wt. %, in particular 10 to 18 wt. %, non-ionic surfactants and/or
1 to 10 wt. %, in particular 1.5 to 3 wt. %, water-soluble or water-dispersible inorganic builder material and/or
0 to 1 wt. %, in particular 0.01 to 0.5 wt. %, fragrances and/or 0.01 to 5 wt. %, in particular 0.05 to 0.5 wt. %, optical brighteners.

Suitable graying inhibitors or soil release active ingredients (soil release polymer) are cellulose ethers, such as carboxymethyl cellulose, methyl cellulose, hydroxyalkyl celluloses and mixed cellulose ethers, such as methyl hydroxyethyl cellulose, methylhydroxypropyl cellulose and methyl carboxymethyl cellulose. Sodium carboxymethyl cellulose, hydroxypropyl methyl cellulose and mixtures thereof and, optionally, mixtures thereof with methyl cellulose are preferably used. The soil release active ingredients commonly used include copolyesters which contain dicarboxylic acid units, alkylene glycol units and polyalkylene glycol units. The proportion of graying inhibitors and/or soil release active ingredients in agents is generally no greater than 2 wt. % and is preferably 0.5 to 1.5 wt. %, particularly preferably 0.5 to 2 wt. %.

Derivatives of diaminostilbene disulfonic acid or the alkali metal salts thereof can be contained, for example, as optical brighteners, in particular for textiles made of cellulose fibers (e.g., cotton). Salts of 4,4'-bis(2-anilino-4-morpholino-1,3,5-triazin-6-ylamino)-stilbene-2,2'-disulfonic acid or similarly constructed compounds that carry a diethanolamino group, a methylamino group or a 2-methoxyethylamino group instead of the morpholino group are suitable, for example. Furthermore, brighteners of the substituted 4,4'-distyryl-diphenyl type can be present, e.g., 4,4'-bis-(4-chloro-3-sulfostyryl)-diphenyl. Mixtures of brighteners can also be used. Brighteners of the 1,3-diaryl-2-pyrazoline type, e.g., 1-(p-sulfoamoylphenyl)-3-(p-chlorophenyl)-2-pyrazoline, and compounds having a similar structure are particularly suitable for polyamide fibers. The content of optical brighteners or brightener mixtures in the agent is generally no greater than 1 wt. %, preferably 0.05 to 0.5 wt. %. In a preferred embodiment, the agent is free of such active ingredients.

The customary foam regulators that can be used in the agents include, for example, polysiloxane-silicic acid mixtures, the finely divided silicic acid contained therein preferably being silanized or otherwise hydrophobized. The polysiloxanes can consist of both linear compounds and crosslinked polysiloxane resins and mixtures thereof. Further defoamers are paraffinic hydrocarbons, in particular microparaffins and paraffin waxes of which the melting point is above 40° C., saturated fatty acids or soaps having in particular 20 to 22 C atoms, for example sodium behenate, and alkali salts of phosphoric acid mono- and/or dialkyl esters, in which the alkyl chains each have 12 to 22 C atoms. Among these, sodium monoalkyl phosphate and/or sodium dialkyl phosphate having $C_{16-18}$ alkyl groups is preferably used. The proportion of foam regulators can preferably be 0.2 to 2 wt. %, particularly preferably not more than 1 wt. %.

In order to set the desired pH, the agents can contain acids that are compatible with the system and environment, in particular citric acid, acetic acid, tartaric acid, malic acid, lactic acid, glycolic acid, succinic acid, glutaric acid, and/or adipic acid, but also mineral acids, in particular sulfuric acid or alkali hydrogen sulfates, or bases, in particular ammonium or alkali hydroxides, preferably sodium hydroxide. These types of pH regulators are contained in the agents in amounts preferably no greater than 10 wt. %, in particular of from 0.5 to 6 wt. %, particularly preferably from 0.3 to 2 wt. %.

Possible peroxygen compounds suitable for use in the agents include, in particular, organic peroxy acids or peracid salts of organic acids, such as phthalimidopercaproic acid, perbenzoic acid, or salts of diperdodecanoic diacid, hydrogen peroxide and inorganic salts giving off hydrogen peroxide under the washing conditions, which salts include perborate, percarbonate, persilicate, and/or persulfates such as caroate, as well as hydrogen peroxide inclusion compounds such as $H_2O_2$-urea adducts. Hydrogen peroxide can also be produced by means of an enzymatic system, i.e., an oxidase and the substrate thereof. If solid peroxygen compounds are intended to be used, these may be used in the form of powders or granules, which may also be coated in a manner known in principle. The peroxygen compounds can be added to the washing liquor as such or in the form of the agents containing them, which in principle can contain all conventional washing, cleaning or disinfectant components. Particularly preferably, alkali percarbonate, or alkali perborate monohydrate is used. If an agent contains peroxygen compounds, these are present in amounts of preferably up to 50 wt. %, in particular from 5 to 30 wt. %, more preferably from 0.1 to 20 wt. %.

Compounds which, under perhydrolysis conditions, result in aliphatic peroxocarboxylic acids having preferably 1 to 10 C atoms, in particular 2 to 4 C atoms, and/or optionally substituted perbenzoic acid, may be used in the agents as bleach activators. Substances that carry the O-acyl and/or N-acyl groups of the stated number of C atoms and/or optionally substituted benzoyl groups are suitable. Preferred are polyacylated alkylene diamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenol sulfonates or carboxylates or the sulfonic or carboxylic acids thereof, in particular nonanoyloxybenzenesulfonate or isononanoyloxybenzenesulfonate or laroyloxybenzenesulfonate (NOBS or iso-NOBS or LOBS), 4-(2-decanoyloxyethoxycarbonyloxy)-benzenesulfonate (DECOBS) or decanoyloxybenzoate (DOBA), carboxylic acid anhydrides, in particular phthalic acid anhydride, acylated polyhydric alcohols, in particular triacetin, ethylene glycol diacetate, 2,5-diacetoxy-2,5-dihydrofuran and enol esters, as well as acetylated sorbitol and mannitol or the described mixtures thereof (SORMAN), acylated sugar derivatives, in particular pentaacetyl glucose (PAG), pentaacetyl fructose, tetraacetylxylose and octaacetyl lactose, acetylated, optionally N-alkylated glucamine and gluconolactone, N-acylated lactams, for example N-benzoylcaprolactam, nitriles from which perimidic acids are formed, in particular aminoacetonitrile derivatives having a quaternized nitrogen atom, and/or oxygen-transferring sulfonimines and/or acylhydrazones. The hydrophilically substituted acyl acetals and the acyl lactams are likewise preferably used. Combinations of conventional bleach activators can also be used. Such bleach activators can, in particular in the presence of the above-mentioned hydrogen peroxide-yielding bleaching agents, be contained in the customary quantity range, preferably in amounts of from 0.5 to 10 wt. %, and in particular 1 to 8 wt. %, based on the total agent, but are preferably entirely absent when percarboxylic acid is used as the sole bleaching agent.

In addition to or instead of the conventional bleach activators, sulfonimines and/or bleach-boosting transition metal salts or transition metal complexes may also be contained in solid agents as what are referred to as bleach catalysts.

The detergents can contain an organic solvent as a further component. Adding organic solvents has an advantageous effect on the enzyme stability and cleaning performance of these agents. Preferred organic solvents are derived from the group of monohydric or polyhydric alcohols, alkanolamines or glycol ethers. The solvents are preferably selected from ethanol, n- or i-propanol, butanol, glycol, propanediol, butanediol, glycerol, diglycol, propylene diglycol, butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether, propylene glycol propyl ether, dipropylene glycol methyl ether, dipropylene glycol ethyl ether, methoxytriglycol, ethoxytriglycol, butoxytriglycol, 1-butoxyethoxy-2-propanol, 3-methyl-3-methoxybutanol, propylene-glycol-t-butyl ether and mixtures of these solvents. The proportion by weight of these organic solvents with respect to the total weight of the detergents is preferably 0.1 to 10 wt. %, more preferably 0.2 to 8.0 wt. % and even more preferably 0.5 to 5.0 wt. %. A particularly preferred organic solvent which is particularly effective in stabilizing the detergents is glycerol, as well as 1,2-propylene glycol. Liquid detergents preferably comprise at least one polyol, preferably from the group glycerol and 1,2-propylene glycol, based on the total weight of the detergent, preferably in an amount of from 0.1 to 10 wt. %, preferably 0.2 to 8.0 wt. % and more preferably 0.5 to 5.0 wt. %. Other preferred organic solvents are the organic amines and alkanolamines. The detergents preferably contain these amines in amounts of from 0.1 to 10 wt. %, more preferably from 0.2 to 8.0 wt. % and even more preferably from 0.5 to 5.0 wt. %, in each case based on the total weight thereof. Ethanolamine is a particularly preferred alkanolamine.

Another preferred component of the detergents is a sugar alcohol (alditol). The group of alditols includes non-cyclic polyols of the formula $HOCH_2[CH(OH)]_nCH_2OH$. The alditols include, e.g., mannitol, isomalt, lactitol, sorbitol and xylitol, threitol, erythritol and arabitol. Sorbitol has been found to be particularly advantageous with regard to enzyme stability. The proportion by weight of the sugar alcohol with respect to the total weight of the detergent is preferably 1.0 to 10 wt. %, more preferably 2.0 to 8.0 wt. % and even more preferably 3.0 to 6.0 wt. %.

Detergents can exclusively contain a protease as defined herein. Alternatively, they may also contain other enzymes in a concentration that is expedient for the effectiveness of the agent. A further embodiment is therefore represented by agents which further comprise one or more additional enzymes. Additional enzymes which can preferably be used are all enzymes which can exhibit catalytic activity in the agent, in particular a lipase, amylase, cellulase, hemicellulase, mannanase, tannase, xylanase, xanthanase, xytoglucanase, β-glucosidase, pectinase, carrageenase, perhydrolase, oxidase, oxidoreductase or another protease, which is different from the proteases, as well as mixtures thereof. Additional enzymes are contained in the agent advantageously in an amount of from $1 \times 10^{-8}$ to 5 wt. %, based on active protein. In order of increasing preference, each additional enzyme is contained in agents in an amount of from $1 \times 10^{-7}$ to 3 wt. %, from 0.00001 to 1 wt. %, from 0.00005 to 0.5 wt. %, from 0.0001 to 0.1 wt. % and particularly preferably from 0.0001 to 0.05 wt. %, based on active protein. Particularly preferably, the enzymes exhibit synergistic cleaning performance against specific stains or spots, i.e., the enzymes contained in the agent composition support one another in their cleaning performance. Very particularly preferably, there is such synergism between the protease contained and an additional enzyme of an agent, including in particular between said protease and an amylase and/or a lipase and/or a mannanase and/or a cellulase and/or a pectinase. Synergistic effects may arise not only between different enzymes, but also between one or more enzymes and other ingredients of the agent. Textile detergents preferred have at least one protease and at least one amylase. In another preferred embodiment, textile detergents have at least one protease and at least one cellulase. In a further preferred embodiment, textile detergents have at least one protease and at least one lipase. Textile detergents which have 3 to 10 different enzymes are particularly preferred, it being possible for textile detergents which have 3 to 10 different types of enzymes to be particularly preferred with regard to the cleaning performance over a very broad spectrum of stains.

Examples of proteases are the subtilisins BPN' from *Bacillus amyloliquefaciens* and Carlsberg from *Bacillus licheniformis*, protease PB92, subtilisins 147 and 309, the protease from *Bacillus lentus*, subtilisin DY, and the enzymes thermitase, proteinase K and proteases TW3 and TW7, which belong to the subtilases but no longer to the subtilisins in the narrower sense. Subtilisin Carlsberg is available in a developed form under the trade name Alcalase® from Novozymes. Subtilisins 147 and 309 are marketed by Novozymes under the trade names Esperase® and Savinase®, respectively. The protease variants are derived from the protease from *Bacillus lentus* DSM 5483. Other proteases that are suitable are, for example, the enzymes available under the trade names Durazym®, Relase®, Everlase®, Nafizym®, Natalase®, Kannase®, Progress Uno 101 L® and Ovozyme® from Novozymes, the enzymes available under the trade names Purafect®, Purafect® OxP, Purafect® Prime, Excellase® and Properase®, Preferenz P100® and Preferenz P300® from Danisco/DuPont, the enzyme available under the trade name Lavergy pro 104 LS® from BASF, the enzyme available under the trade name Protosol® from Advanced Biochemicals Ltd., the enzyme available under the trade name Wuxi® from Wuxi Snyder Bioproducts Ltd., the enzymes available under the trade names Proleather® and Protease P® from Amano Pharmaceuticals Ltd., and the enzyme available under the name Proteinase K-16 from Kao Corp. The proteases from *Bacillus gibsonii* and *Bacillus pumilus* which are disclosed in international patent applications WO 2008/086916 A1 and WO 2007/131656 A1 are particularly preferably used. Further proteases which can be used advantageously are disclosed in the patent applications WO 91/02792 A1, WO2008/007319 A2, WO 93/18140 A1, WO 01/44452 A1, GB 1243784 A, WO 96/34946 A1, WO 02/029024 A1 and WO 03/057246 A1. Further proteases that can be used are those which are naturally present in the microorganisms *Stenotrophomonas maltophilia*, in particular *Stenotrophomonas maltophilia* K279a, *Bacillus intermedius* and *Bacillus sphaericus*.

Examples of amylases are α-amylases from *Bacillus licheniformis*, from *Bacillus amyloliquefaciens* or from *Bacillus stearothermophilus*, as well as in particular the developments thereof that have been improved for use in washing or cleaning agents. The enzyme from *Bacillus licheniformis* is available from Novozymes under the name Termamyl® and from Danisco/DuPont under the name Purastar® ST. Development products of this α-Amylase are available under the trade names Duramyl® and Termamyl® ultra (both from Novozymes), Purastar® OxAm (Danisco/DuPont) and Keistase® (Daiwa Seiko Inc.). The α-amylase from *Bacillus amyloliquefaciens* is marketed by Novozymes under the name BAN®, and derived variants from the α-amylase from *Bacillus stearothermophilus* are marketed under the names BSG® and Novamyl®, also by Novozymes. Furthermore, for this purpose the α-amylases from *Bacillus* sp. A 7-7 (DSM 12368) and the cyclodextrin glucanotransferase (CGTase) from *Bacillus agaradherens* (DSM 9948) should be emphasized. Furthermore, amylolytic enzymes which are disclosed in the international patent applications WO 95/26397 A1, WO 96/23873 A1, WO 99/23211 A1, WO 00/60060 A2, WO 03/002711 A2, WO 03/054177 A2, WO 2006/002643 A2, WO 2007/079938 A2, WO 2011/100410 A2 and WO 2013/003659 A1 can be used. Fusion products of all mentioned molecules can also be used. Furthermore, the developments of the α-amylase from *Aspergillus niger* and *A. oryzae*, available under the trade name Fungamyl® from Novozymes, are suitable. Other commercial products that can be advantageously used are, for example, Amylase-LT® and Stainzyme® or Stainzyme® ultra or Stainzyme® plus as well as Amplify™ 12L or Amplify Prime™ 100L, the latter also from Novozymes, and the PREFERENZ S® series from Danisco/DuPont, including, for example, PREFERENCE S100®, PREFERENCE S1000® or PREFERENCE S210®. Variants of these enzymes that can be obtained by point mutations can also be used.

Preferred amylases comprise a) an α-amylase which comprises an amino acid sequence which is at least 80% and, in order of increasing preference, at least 81%, 82, 83%, 84%, 85%, 86%, 87%, 88%, 89%, 90%, 91%, 92%, 93%, 94%, 95%, 96%, 97%, 98%, 99% identical to the amino acid sequence given in SEQ ID NO:2 over its entire length and has at least one amino acid substitution at one of the positions 172, 202, 208, 255 and 261 in the numbering according to SEQ ID NO:2, preferably selected from the group consisting of M202L, M202V, M202S, M202T, M202I, M202Q, M202W, S255N, R172Q, and combinations thereof. More preferably, the amylase comprises the amino acid substitution M202L or M202T.

Further preferred amylases comprise b) an α-amylase which comprises an amino acid sequence which is at least 60% and, in order of increasing preference, at least 70%, 75%, 80%, 81%, 82%, 83%, 84%, 85%, 86%, 87%, 88%, 89%, 90%, 91%, 92%, 93%, 94%, 95%, 96%, 97%, 98%, 99% identical to the amino acid sequence given in SEQ ID NO:3 over its entire length and has at least one amino acid substitution at one of the positions 9, 26, 30, 33, 82, 37, 106, 118, 128, 133, 149, 150, 160, 178, 182, 186, 193, 195, 202, 203, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482 and 484 and/or a deletion at one of the positions 183 and 184 in the numbering according to SEQ ID NO:3. Particularly preferred amylases have at least one amino acid substitution at one of the positions 9, 26, 149, 182, 186, 202, 257, 295, 299, 323, 339 and 345, and/or particularly preferably at least one amino acid substitution or deletion that is selected from the group consisting of R118K, D183*, G184*, N195F, R320K, R458K and combinations thereof. Very particularly preferred amylases comprise an amino acid sequence which is at least 60% and, in order of increasing preference, at least 70%, 75%, 80%, 81%, 82%, 83%, 84%, 85%, 86%, 87%, 88%, 89%, 90%, 91%, 92%, 93%, 94%, 95%, 96%, 97%, 98%, 99% identical to the amino acid sequence given in SEQ ID NO:3 over its entire length, and have one of the following amino acid substitution or deletion combinations:

(i) M9L+M323T;
(ii) M9L+M202LZTZVZI+M323T;
(iii) M9L+N195F+M202LZTZVZI+M323T;
(iv) M9L+R118K+D183*+G184*+R320K+M323T+R458K;
(v) M9L+R118K+D183*+G184*+M202L/T/V/I+R320K+M323T+R458K;
(vi) M9L+G149A+G182T+G186A+M202L+T257I+Y295F+N299Y+M323T+A339 S+E345R;
(vii) M9L+G149A+G182T+G186A+M202I+T257I+Y295F+N299Y+M323T+A339 S+E345R;
(viii) M9L+R118K+G149A+G182T+D183*+G184*+G186A+M202L+T257I+Y295F+N299Y+R320K+M323T+A339S+E345R+R458K;
(ix) M9L+R118K+G149A+G182T+D183*+G184*+G186A+M202I+T257I+Y295F+N299Y+R320K+M323T+A339S+E345R+R458K;
(x) M9L+R118K+D183*+D184*+N195F+M202L+R320K+M323T+R458K;
(xi) M9L+R118K+D183*+D184*+N195F+M202T+R320K+M323T+R458K;
(xii) M9L+R118K+D183*+D184*+N195F+M202I+R320K+M323T+R458K;
(xiii) M9L+R118K+D183*+D184*+N195F+M202V+R320K+M323T+R458K;
(xiv) M9L+R118K+N150H+D183*+D184*+N195F+M202L+V214T+R320K+M323 T+R458K;
(xv) M9L+R118K+D183*+D184*+N195F+M202L+V214T+R320K+M323T+E345N+R458K.

Further preferred amylases comprise c) an α-amylase which comprises an amino acid sequence which is at least 90% identical to the amino acid sequence given in SEQ ID NO:4 over its entire length and optionally has at least one substitution and/or deletion at one of the positions 93, 116, 118, 129, 133, 134, 140, 142, 146, 147, 149, 151, 152, 169, 174, 183, 184, 186, 189, 193, 195, 197, 198, 200, 203, 206, 210, 212, 213, 235, 243, 244, 260, 262, 284, 303, 304, 320, 338, 347, 359, 418, 431, 434, 439, 447, 458, 469, 476 and 477 in the numbering according to SEQ ID NO:4, preferably amino acid deletions at the positions 183 and 184. Preferred amino acid substitutions comprise E260A/D/C/Q/L/M/F/P/S/W/V/G/H/I/K/N/R/T/Y, G304RZKZEZQ, W140Y/F, W189E/G/T, D134E, F262G/P, W284D/H/F/Y/R, W347H/F/Y, W439R/G, G476E/Q/R/K, G477E/Q/K/M/R, N195F/Y, N197F/L, Y198N, Y200F, Y203F, I206H/L/N/F/Y, H210Y, E212V/G, V213A, M116T, Q129L, G133E, E134Y, K142R, P146S, G147E, G149R, N151R, Y152H, Q169E, N174R, A186R, Y243F, S244Q, G303V, R320N, R3591, N418D and A447V.

Examples of cellulases (endoglucanases, EG) include the fungal cellulase preparation which is rich in endoglucanase (EG) and the developments thereof which are provided by Novozymes under the trade name Celluzyme®. The products Endolase® and Carezyme®, also available from Novozymes, are based on 50 kD-EG and 43 kD-EG, respectively, from *Humicola insolens* DSM 1800. Further commercial products from this company that can be used are Cellusoft®, Renozyme®, and Celluclean®. It is also possible to use cellulases, for example, which are available from AB Enzymes under the trade names Ecostone® and Biotouch®, and which are, at least in part, based on 20 kD-EG from *Melanocarpus*. Further cellulases from AB Enzymes are Econase® and Ecopulp®. Further suitable cellulases are from *Bacillus* sp. CBS 670.93 and CBS 669.93, with the cellulase from *Bacillus* sp. CBS 670.93 being available from Danisco/DuPont under the trade name Puradax®. Further commercial products that can be used from Danisco/DuPont are "Genencor detergent cellulase L" and IndiAge® Neutra.

Further enzymes that can be used are, for example, lipases or cutinases, in particular for the triglyceride-cleaving activities thereof, but also so as to create peroxy acids in situ from suitable precursors. These include, for example, the lipases that can originally be obtained from *Humicola lanuginosa* (*Thermomyces lanuginosus*) or have been developed therefrom, in particular those having one or more of the following amino acid exchanges in the positions D96L, T213R and/or N233R, particularly preferably T213R and N233R, proceeding from the mentioned lipase. Lipases are sold, for example, by the Novozymes company under the trade names Lipolase®, Lipolase® Ultra, LipoPrime®, Lipozyme® and Lipex®. Another lipase that can be used advantageously is available from Novozymes under the trade name Lipoclean®. Moreover, the cutinases which have been originally isolated from *Fusarium solani pisi* and *Humicola insolens* can also be used, for example. Lipases that are also suitable are available from Amano under the names Lipase CE®, Lipase P®, Lipase B® or Lipase CES®, Lipase AKG®, *Bacillus* sp. Lipase®, Lipase AP®, Lipase M-AP® and Lipase AML®. From the company Danisco/DuPont, for example, lipases or cutinases can be used of which the starting enzymes were originally isolated from *Pseudomonas mendocina* and *Fusarium solanii*. The preparations M1 Lipase® and Lipomax® marketed by Danisco/Genencor, the enzymes marketed by Meito Sangyo KK, under the names Lipase MY-30®, Lipase OF® and Lipase PL®, and the product Lumafast® from Danisco/DuPont should be mentioned as other important commercial products.

In order to increase the bleaching effect, oxidoreductases such as oxidases, oxygenases, catalases, peroxidases such as halo-, chloro-, bromo-, lignin, glucose, or manganese peroxidases, dioxygenases or laccases (phenoloxidases, polyphenoloxidases) can be used. Advantageously, organic, particularly preferably aromatic compounds that interact with the enzymes are additionally added in order to potentiate the activity of the relevant oxidoreductases (enhancers) or, in the event of greatly differing redox potentials, to ensure the flow of electrons between the oxidizing enzymes and the stains (mediators).

The enzymes to be used within the context can originate, for example, from microorganisms such as the genera *Bacillus*, *Streptomyces*, *Humicola* or *Pseudomonas* and/or be produced by suitable microorganisms using biotechnological methods known per se, for example by transgenic expression hosts, for example of the genera *Escherichia* or *Bacillus*, or by filamentous fungi. It is emphasized that in particular technical enzyme preparations of the relevant enzyme can also be involved, i.e., accompanying substances can be present. Therefore, the enzymes can be packaged and used together with accompanying substances, for example from fermentation or with other stabilizers.

An agent advantageously contains the protease in an amount of from 2 µg to 20 mg, preferably from 5 µg to 17.5 mg, particularly preferably from 20 µg to 15 mg and most particularly preferably from 50 µg to 10 mg per gram of the agent. In various embodiments, the concentration of the protease (active enzyme) described herein in the agent is >0 to 1 wt. %, preferably 0.001 to 0.1 wt. %, based on the total weight of the agent.

Further, the protease contained in the agent, and/or other ingredients of the agent, may be coated with a substance which is impermeable to the enzyme at room temperature or in the absence of water, and which becomes permeable to the enzyme under conditions of use of the agent. Such an embodiment is thus characterized in that the protease is coated with a substance which is impermeable to the protease at room temperature or in the absence of water. Furthermore, the detergent itself can be packed in a container, preferably an air-permeable container, from which it is released shortly before use or during the washing process.

The protease and/or optionally additional enzymes of the same or different type contained in the detergent can be adsorbed on carrier materials and/or embedded in coating substances in order to protect them against premature inactivation. The enzyme is then released in the washing liquor, i.e., under application conditions, and can develop its catalytic effect. Preferred packaging forms have 0.05 to 15 wt. % and in particular up to 10 wt. % active protein of the protease mentioned.

A detergent contains the protease, in order of increasing preference, in an amount of from $1 \times 10^{-8}$ to 5 wt. %, from 0.0001 to 1 wt. %, from 0.0005 to 0.5 wt. %, from 0.001 to 0.1 wt. %, in each case based on active protein.

In the agents described herein, the enzymes to be used may furthermore be formulated together with accompanying substances, for example from fermentation. In liquid formulations, the enzymes are preferably used as enzyme liquid formulations. The enzymes are generally not provided in the form of pure protein, but rather in the form of stabilized, storable and transportable preparations. These pre-packaged preparations include, e.g., the solid preparations obtained through granulation, extrusion, or lyophilization or, in particular in the case of liquid or gel agents, solutions of the enzymes, which are advantageously maximally concentrated, have a low water content, and/or are supplemented with stabilizers or other auxiliaries. Alternatively, the enzymes can also be encapsulated, for both the solid and the liquid administration form, e.g., by spray-drying or extrusion of the enzyme solution together with a preferably natural polymer or in the form of capsules, e.g., those in which the enzymes are enclosed in a set gel, or in those of the core-shell type, in which an enzyme-containing core is coated with a water-, air-, and/or chemical-impermeable protective layer. Other active ingredients such as stabilizers, emulsifiers, pigments, bleaching agents, or dyes can additionally be applied in overlaid layers. Such capsules are applied using methods that are known per se, for example by shaking or roll granulation or in fluidized bed processes. Advantageously, such granules are low in dust, for example due to the application of polymeric film-formers, and stable in storage due to the coating. Moreover, it is possible to formulate two or more enzymes together such that a single granule exhibits a plurality of enzyme activities.

The enzymes can also be incorporated in water-soluble films, such as those used in the formulation of detergents in a unit dosage form. Such a film allows the release of the enzymes following contact with water. As used herein, "water-soluble" refers to a film structure that is preferably completely water-soluble. Preferably, such a film consists of (fully or partly hydrolyzed) polyvinyl alcohol (PVA).

The embodiments include all solid, powdered, granular, tablet-form, liquid, gel or pasty administration forms of agents, which may optionally also consist of a plurality of phases and can be present in compressed or uncompressed form. The agent may be present as a flowable powder, in particular having a bulk density of from 300 to 1,200 g/l, in particular 500 to 900 g/l or 600 to 850 g/l. The solid dosage forms of the agent also include extrudates, granules, tablets or pouches containing solid agents, which can be present both in large containers and in portions. Alternatively, the agent may also be in liquid, gel or pasty form, for example in the form of a non-aqueous liquid detergent or a non-aqueous paste or in the form of an aqueous liquid detergent or a water-containing paste. The agent may also be present as a single-component system. Such agents consist of one phase. Alternatively, an agent may also consist of a plurality of phases (multi-component system). Such an agent is accordingly divided into several components, for example two liquid, two solid or one liquid and one solid phase. The liquid presentation forms based on water and/or organic solvents can be present in thickened form, in the form of gels.

A substance, e.g., a composition or an agent, is solid if it is in a solid state of aggregation at 25° C. and 1,013 mbar.

A substance, e.g., a composition or an agent, is liquid if it is in a liquid state of aggregation at 25° C. and 1,013 mbar. Liquid also includes gel form.

If the detergents are in liquid form, they preferably contain more than 40 wt. %, preferably 50 to 90 wt. % and particularly preferably 60 to 80 wt. %, water, based on their total weight.

The disclosure also relates to a method for cleaning textiles, in which method a textile detergent, in particular a liquid textile detergent, is used in at least one method step. This includes both manual and machine methods, with machine methods being preferred because they can be controlled more precisely, for example with regard to the quantities used and contact times. Methods for cleaning textiles are generally characterized by the fact that, in one or more method steps, various cleaning-active substances are applied to the material to be cleaned and washed off after the exposure time, or in that the material to be cleaned is otherwise treated with a detergent or a solution or dilution of this agent.

In various embodiments, the method is characterized in that the protease is used at a temperature of 0 to 100° C., preferably 10 to 70° C., more preferably 30 to 50° C. and most preferably at 20 to 40° C. In particular, in methods which are carried out at a temperature between 10 and 60° C., preferably between 15 and 50° C. and more preferably between 20 and 40° C., the advantages of using the textile detergent compared with textile detergents comprising conventionally used proteases for the consumer can be seen.

All elements, subjects and embodiments described for textile detergents are also applicable to this subject of the disclosure. Therefore, reference is expressly made at this point to the disclosure at the corresponding point when it was indicated that this disclosure also applies to the above-described methods.

Alternative embodiments also include methods for treating textile raw materials or for textile care in which a protease becomes active in at least one method step. Among these, methods for textile raw materials, fibers or textiles comprising natural constituents are preferred, and very particularly for such materials, fibers or textiles comprising wool or silk.

The proteases used in detergents can advantageously be used in accordance with the above statements in textile detergents and methods for washing textiles. They can thus be used advantageously to provide proteolytic activity in corresponding agents and methods.

Finally, the disclosure also encompasses the use of the proteases described herein in detergents, for example as described above, for the (improved) removal of protease-sensitive stains, for example from textiles. In preferred embodiments of this use, the protease is stored in the detergent for 3 or more days, 4 or more days, 7 or more days, 10 or more days, 12 or more days, 14 or more days, 21 or more days or 28 or more days prior to a wash.

The disclosure therefore further relates to
the use of an agent for cleaning textiles, and/or
the use of a protease comprising an amino acid sequence which has at least 70% sequence identity with the amino acid sequence given in SEQ ID NO: 1 over its entire length and, in each case based on the numbering according to SEQ ID NO: 1, has (i) at at least two of the positions that correspond to positions 3, 4, 99 or 199, at least two amino acid substitutions, in particular the amino acid substitutions 3T, 4I, 99E and 199I, and (ii) at at least one of the positions that correspond to positions 74, 136, 143, 154, 161, 163, 171, 200, 203, 209, 212 or 256, at least one additional amino acid substitution, in particular selected from N74D, N74E, N74Q, A136Q, R143L, R143W, R143Y, S154D, S154Q, Y161T, A163G, V171L, Q200A, Q200L, Q200S, Q200T, Y203K, Y203V, Y203W, A209W, N212S, N212T, 256D, L256E and L256Q, in a textile detergent, preferably a liquid textile detergent, for removing protease-sensitive stains on textiles, the textile detergent having a pH of from approximately 9 to approximately 12, measured in a 1 wt. % solution in deionized water at 20° C.,
in particular such that the protease is used in each case in an amount of from 2 µg to 20 mg, preferably from 5 µg to 17.5 mg, particularly preferably from 20 µg to 15 mg and most particularly preferably from 50 µg to 10 mg per gram of the agent.

Particularly preferred embodiments are, for example, hand washing, the manual removal of stains from textiles or use in connection with a machine process.

All elements, subjects and embodiments that are described for proteases and agents that contain them can also be applied to this subject of the disclosure. Express reference is therefore made here to the disclosure at the corresponding point when it was indicated that this disclosure also applies to the above-described use.

EXAMPLES

Determination of Storage Stability in Liquid Detergent Detergent Matrix Used

Commercially available liquid detergents as indicated in table 1 were used.

TABLE 1a

Formula A

| Ingredient | Formula A (in wt. %) |
| --- | --- |
| Citric acid | 1-4% |
| Anti-foaming agents | <1% |
| FAEOS (anionic surfactant) | 2-5% |
| FAEO (non-ionic surfactant) | 5-9% |
| LAS (anionic surfactant) | 7-12% |
| Palm kernel oil fatty acids | 1-3% |
| Monoethanolamine | 2-6% |
| NaOH 50% | 0.3-2% |
| Glycerol | 0.5-3% |
| 1,2-Propanediol | 4-8% |
| HEDP | 0.5-2% |
| soil release polymer | 0.2-1% |
| Boric acid | 0.5-1.5% |
| Demineralized water | to make up to 100% |

Without fragrances, enzymes and optical brighteners; dosage 3.17 g/L
The pH of formula A, measured in a 1 wt. % solution in deionized water at 20° C., is pH 10.

TABLE 1b

Formula B

| Ingredient | Formula B (in wt. %) |
| --- | --- |
| LAS (anionic surfactant) | 3% |
| Alcohol ethoxylate 7EO | 2% |
| Alcohol ether sulfate 3EO | 8% |
| coconut fatty acids | 0.5% |
| NaOH 50% | 0.4% |
| Sodium carbonate | 3% |
| Distyrbiphenyl disulfonate | 0.05% |
| Fragrances | 0.5% |
| Demineralized water & misc. | |

The pH of formula B, measured in a 1 wt. % solution in deionized water at 20° C., is pH 11.

The following proteases have been used:
C1: Protease according to SEQ ID NO:2 from WO 2013/060621 A1
C2: Subtilisin 309 from *Bacillus lentus*
E1: SEQ ID NO:1+S3T+V4I+R99E+V199I+Q200L+Y203W;
E2: SEQ ID NO:1+S3T+V4I+R99E+V199I+Q200L+Y203W+S154D+L256E;

Storage

The proteases are present in *Bacillus licheniformis* in supernatants generated in a bioreactor. Said proteases are diluted to the same activity level. 90% detergent matrix (formula A or formula B) was mixed with 10% appropriately diluted *Bacillus licheniformis* supernatant and mixed well. The enzyme activity in each batch was determined (starting value) before the sealed vessels were stored at 30° C. or 40° C. for two weeks, four weeks or ten weeks. The amount of sample taken was dissolved in 0.1 M Tris/HCl (pH 8.6) by stirring at room temperature for 20 min. The AAPF assay was then carried out as described below.

Protease Activity Assay (AAPF Assay)

The activity of the protease is determined by the release of the chromophore para-nitroaniline from the substrate succinyl alanine-alanine-proline-phenylalanine-para-nitroanilide (AAPFpNA; Bachem L-1400). The release of the pNA causes an increase in absorbance at 410 nm, the temporal progression of which is a measure of the enzymatic activity.

The measurement was carried out a temperature of 25° C., a pH of 8.6, and a wavelength of 410 nm. The measuring time was 5 minutes with a measuring interval of from 20 to 60 seconds.

Measurement Approach:
10 µL AAPF solution (70 mg/mL)
1000 µL Tris/HCl (0.1 M, pH 8.6 with 0.1% Brij 35)
10 µL diluted protease solution
Kinetics created over 5 min at 25° C. (410 nm)

Results

The residual activity in % after storage in the above-mentioned detergent matrix is shown below. The residual activity in % is based on the relevant enzyme activity before storage (starting value).

TABLE 2

Storage in formula A (pH 10) at 30° C. or 40° C. for two weeks

| | Residual activity (%) | |
| --- | --- | --- |
| Protease | 30° C. | 40° C. |
| C1 | 14 | 0 |
| E1 | 85 | 52 |
| E2 | 51 | 77 |

TABLE 3

Storage in formula B (pH 10; adjusted by adding citric acid) at 30° C. or 40° C. for two weeks

| | Residual activity (%) | |
| --- | --- | --- |
| Protease | 30° C. | 40° C. |
| C1 | 18 | 3 |
| C2 | 9 | 0 |
| E1 | 66 | 42 |
| E2 | 100 | 100 |

TABLE 4

Storage in formula B (pH 11) at 30° C. for two, four or ten weeks

| | Residual activity (%) | | |
| --- | --- | --- | --- |
| Protease | 2 weeks | 4 weeks | 10 weeks |
| C1 | 5 | 0 | 0 |
| E2 | 56 | 48 | 19 |

The proteases E1 and E2 demonstrate significantly higher storage stability than the comparison proteases C1 and C2 in various highly alkaline detergent formulations, when stored both at 30° C. and at 40° C. for 2 to 10 weeks.

The invention claimed is:

1. A textile washing agent, comprising:
   a) at least one protease, wherein the protease has proteolytic activity and comprises an amino acid sequence which has at least 80% sequence identity with the amino acid sequence as set forth in SEQ ID NO: 1 over its entire length and, in each case based on the numbering according to SEQ ID NO: 1, has
      (i) amino acid substitutions 99E and 154D,
      (ii) optionally comprising at least one additional amino acid substitution at the position corresponding to positions 3, 4 or 199, and
      (iii) optionally comprising at least one additional amino acid substitution at the position corresponding to position 74, 136, 143, 161, 163, 171, 200, 203, 209, 212 or 256; and
   b) at least one washing agent ingredient;
   wherein the textile washing agent has a pH ranging from approximately 9 to approximately 12, measured at 20° C. in 1 wt. % solution in deionized water.

2. The textile washing agent according to claim 1, wherein the protease comprises substitutions (i) S3T, V4I, and V199I, and (ii) at least one additional amino acid substitution selected from the group consisting of N74D, N74E, N74Q, A136Q, R143L, R143W, R143Y, Y161T, A163G, V171L, Q200A, Q200L, Q200S, Q200T, Y203K, Y203V, Y203W, A209W, N212S, N212T, L256D, L256E, and L256Q.

3. The textile washing agent according to claim 1, wherein the protease has one of the following amino acid substitution variants, in each case based on the numbering according to SEQ ID NO: 1:
   (i) S3T+V4I+V199I+Q200L+Y203W;
   (ii) S3T+V4I+V199I+N212S;
   (iii) S3T+V4I+V199I+N74D;
   (iv) S3T+V4I+V199I+L256E;
   (v) S3T+V4I+V199I+Q200L+Y203W+L256E;
   (vi) S3T+V4I+V199I+N74D+Q200L+Y203W;
   (vii) S3T+V4I+V199I+N74D+Q200L+Y203W+L256E;
   (viii) S3T+V4I+V199I+N74D+N212S;
   (ix) S3T+V4I+V199I+N74D+Y203W+L256E;
   (x) S3T+V4I+V199I+N74D+Y203W;
   (xi) S3T+V4I+V199I+N74D+Q200L+L256E;
   (xii) S3T+V4I+V199I+N74D+Q200L;
   (xiii) S3T+V4I+V199I+Q200L+Y203 W;
   (xiv) S3T+V4I+V199I+Q200L+Y203W+L256E;
   (xv) S3T+V4I+V199I+A136Q+R143W+Y161T+Q200L;
   (xvi) S3T+V4I+V199I+N74D+R143Y+A209W+N212S+L256E; or
   (xvii) S3T+V4I+V199I+A136Q+V171L+Q200L.

4. The textile detergent according to claim 1, wherein the protease is present in an amount ranging from $1\times10^{-8}$ to 5 wt. % based on the total weight of the textile detergent.

5. The textile detergent according to claim 1, further comprising at least one additional enzyme selected from the group consisting of amylases, cellulases, hemicellulases, mannanases, tannases, xylanases, xanthanases, xyloglucanases, β-glucosidases, pectinases, carrageenases, perhydrolases, oxidases, oxidoreductases, lipase, and combinations thereof.

6. The textile detergent according to claim 5, wherein the at least one additional enzyme is an amylase and wherein the at least one amylase is selected from:
   a) an α-amylase which comprises an amino acid sequence which is at least 80% identical to the amino acid sequence as set forth in SEQ ID NO:2 over its entire length and optionally has at least one amino acid substitution at one of the positions 172, 202, 208, 255, 261, and combinations thereof in the numbering according to SEQ ID NO: 2;
   b) an α-amylase which comprises an amino acid sequence which has at least 60% identity with the amino acid sequence as set forth in SEQ ID NO:3 over its entire length and optionally has at least one amino acid substitution at one of the positions 9, 26, 30, 33, 82, 37, 106, 118, 128, 133, 149, 150, 160, 178, 182, 186, 193, 195, 202, 203, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482, 484, and combinations thereof, and/or a deletion at one of the positions 183 and 184 in the numbering according to SEQ ID NO:3;
   c) an a-amylase which comprises an amino acid sequence which is at least 90% identical to the amino acid sequence as set forth in SEQ ID NO: 4 over its entire length and optionally has at least one substitution and/or deletion at one or more of positions 93, 116, 118, 129, 133, 134, 140, 142, 146, 147, 149, 151, 152, 169, 174, 184, 186, 189, 193, 195, 197, 198, 200, 203, 206, 210, 212, 213, 235, 243, 244, 262, 284, 303, 304, 320, 338, 347, 359, 418, 431, 434, 439, 447, 458, 469, 476, and 477 in the numbering according to SEQ ID NO: 4; and
   d) combinations thereof.

7. The textile washing agent according to claim 1, wherein the detergent ingredient is selected from the group consisting of surfactants, builders, complexing agents, polymers, glass corrosion inhibitors, corrosion inhibitors, bleaching agents, peroxygen compounds, bleach activators or bleach catalysts, water-miscible organic solvents, enzyme stabilizers, sequestering agents, electrolytes, pH regulators, optical brighteners, graying inhibitors, dye transfer inhibitors, foam regulators, dyes, fragrances, and combinations thereof.

8. The textile detergent according to claim 1, wherein the detergent ingredient comprises:
   a) one or more anionic surfactants in an amount ranging from 5 to 20 wt. %;
   b) one or more non-ionic surfactants in an amount ranging from 1 to 20 wt. %;
   c) one or more water-soluble organic builder substances in an amount ranging from 0.5 to 10 wt. %;
   d) one or more complexing agents in an amount ranging from 0.01 to 5 wt. %;
   e) one or more graying inhibitors in an amount ranging from 0.01 to 5 wt. %;
   f) one or more suds suppressors in an amount ranging from 0.01 to 5 wt. %;
   g) combinations thereof.

9. The textile detergent according to claim 1, wherein the detergent ingredient comprises:
   a) one or more anionic surfactants in an amount ranging from 1 to 10 wt. %;
   b) one or more non-ionic surfactants in an amount ranging from 5 to 20 wt. %;
   c) one or more water-soluble or water-dispersable inorganic builder substances in an amount ranging from 1 to 10 wt. %;
   d) one or more fragrances in an amount ranging from 0.01 to 1 wt. %;
   e) one or more optical brighteners in an amount ranging from 0.01 to 5 wt. %; and
   f) combinations thereof.

10. The textile washing agent according to claim 1, wherein the pH ranges from approximately 9.5 to approximately 11.5, in a 1 wt. % solution in deionized water at 20° C.

11. A method for cleaning textiles, wherein the method comprises:
    applying the textile detergent according to claim 1 to a textile.

12. The method according to claim 11, wherein an increased amount of protease-sensitive stains are removed from the textile as compared to a textile in the absence of the textile detergent.

* * * * *